(12) United States Patent
Coulibaly et al.

(10) Patent No.: US 10,682,407 B2
(45) Date of Patent: *Jun. 16, 2020

(54) CONSTRAINED IMMUNOGENIC COMPOSITIONS AND USES THEREFOR

(71) Applicant: MONASH UNIVERSITY, Clayton (AU)

(72) Inventors: Fasseli Joseph Coulibaly, Burwood East (AU); Ashley Scott Mansell, Croydon (AU); Rosemary Ann Ffrench, Kyneton (AU)

(73) Assignee: Monash University, Clayton (AU)

( * ) Notice: Subject to any disclaimer, the term of this patent is extended or adjusted under 35 U.S.C. 154(b) by 326 days.

This patent is subject to a terminal disclaimer.

(21) Appl. No.: 15/232,736

(22) Filed: Aug. 9, 2016

(65) Prior Publication Data

US 2017/0000878 A1    Jan. 5, 2017

Related U.S. Application Data

(62) Division of application No. 13/806,117, filed as application No. PCT/AU2011/000763 on Jun. 23, 2011, now abandoned.

(Continued)

(51) Int. Cl.
*A61K 39/385*   (2006.01)
*A61K 39/21*    (2006.01)
(Continued)

(52) U.S. Cl.
CPC ............. *A61K 39/21* (2013.01); *A61K 35/76* (2013.01); *A61K 39/12* (2013.01); *A61K 39/15* (2013.01);
(Continued)

(58) Field of Classification Search
None
See application file for complete search history.

(56) References Cited

U.S. PATENT DOCUMENTS 4,816,567 A    3/1989   Cabilly et al. ............... 530/387
4,870,023 A †  9/1989   Fraser
(Continued)

FOREIGN PATENT DOCUMENTS

EP    0 577 894    11/1992
EP    1 582 589    3/2010
(Continued)

OTHER PUBLICATIONS

Letter/Written Disclosure of the Supplemental Information Disclosure Statement for the above-referenced application, filed herewith on Apr 23, 2018, 2 pages.

(Continued)

*Primary Examiner* — M Franco G Salvoza
(74) *Attorney, Agent, or Firm* — Dentons US LLP; Stephanie Seidman

(57) ABSTRACT

A stable immunogenic or vaccine composition comprising a complex or polyhedra comprising same comprising an antigen of a pathogen or other antigen against which a immune response is sought in a human or non-human animal subject and a polyhedrin protein derived from a cytoplasmic polyhedrosis virus (CPV). Delivery of the complex to a subject in substantially polyhedral form induces an immune response thereto. Methods of using same to elicit an immune response.

13 Claims, 24 Drawing Sheets

Immobilisation of Gag into polyhedra

Related U.S. Application Data

(60) Provisional application No. 61/357,667, filed on Jun. 23, 2010.

(51) Int. Cl.

| | | |
|---|---|---|
| *A61K 35/76* | (2015.01) | |
| *A61K 39/12* | (2006.01) | |
| *A61K 39/15* | (2006.01) | |
| *C12N 7/00* | (2006.01) | |
| *A61K 39/00* | (2006.01) | |

(52) U.S. Cl.
CPC .............. *A61K 39/385* (2013.01); *C12N 7/00* (2013.01); *A61K 2039/5258* (2013.01); *A61K 2039/545* (2013.01); *A61K 2039/57* (2013.01); *A61K 2039/575* (2013.01); *A61K 2039/6075* (2013.01); *A61K 2039/70* (2013.01); *C12N 2720/12023* (2013.01); *C12N 2720/12034* (2013.01); *C12N 2740/16234* (2013.01)

(56) References Cited

U.S. PATENT DOCUMENTS

| | | | |
|---|---|---|---|
| 4,873,192 A | 10/1989 | Kunkel et al. | 435/172.3 |
| 5,443,828 A | 8/1995 | Kang et al. | 424/188.1 |
| 7,282,353 B2 * | 10/2007 | Chao | C12N 7/00 435/69.7 |
| 7,319,000 B1 * | 1/2008 | Sastry | A61K 38/162 435/5 |
| 7,432,347 B2 | 10/2008 | Ohta et al. | 530/350 |
| 7,619,060 B2 | 1/2009 | Ikeda | 530/350 |
| 8,554,493 B2 | 10/2013 | Metcalf et al. | 702/27 |
| 9,079,950 B2 | 7/2015 | Drummer et al. | 424/228.1 |
| 2004/0059091 A1 | 3/2004 | Ohta et al. | 530/350 |
| 2005/0048075 A1 | 3/2005 | Chao et al. | 424/186.1 |
| 2006/0053498 A1 | 3/2006 | Bejanin et al. | 800/8 |
| 2006/0155114 A1 | 7/2006 | Ikeda et al. | 530/350 |
| 2010/0216651 A1 | 8/2010 | Metcalf et al. | 506/7 |
| 2013/0171129 A1 | 7/2013 | Coulibaly et al. | 424/130.1 |
| 2013/0323282 A1 | 12/2013 | Drummer et al. | 424/228.1 |

FOREIGN PATENT DOCUMENTS

| | | |
|---|---|---|
| EP | 2 183 013 | 3/2013 |
| JP | H02-502876 | 9/1990 |
| JP | 2008-001610 | 1/2008 |
| JP | 2010-535094 | 11/2010 |
| WO | WO 1988/007082 | 9/1988 |
| WO | WO 1996/11698 | 4/1996 |
| WO | WO 2002/036785 | 5/2002 |
| WO | WO 2003/047617 | 6/2003 |
| WO | WO 2004/063371 | 7/2004 |
| WO | WO 2008/105672 | 9/2008 |

OTHER PUBLICATIONS

Examination Report, dated Nov 20, 2015, in connection with corresponding Australian Patent Application No. 2011269729, 3 pages.
Response, filed Nov 15, 2016, to Examination Report, dated Nov 20, 2015, in connection with corresponding Australian Patent Application No. 2011269729, 13 pages.
Notice of Acceptance, dated Nov. 24, 2016, in connection with corresponding Australian Patent Application No. 2011269729, 2 pages.
Examination Report, dated Oct. 26, 2016, in connection with corresponding Canadian Patent Application No. 2,803,029, 4 pages.
Matsushima et al., "Secreted Frizzled Related Protein 4 Reduces Fibrosis Scar Size and Ameliorates Cardiac Function After Ischemic Injury," Tissue Engineering: Part A 16(11):3329-3341 (2010).
Letter/Written Disclosure of the Information Disclosure Statement for the above-referenced application, filed herewith on Oct. 21, 2016, 2 pages.
Altschul et al., "Gapped BLAST and PSI-BLAST: a new generation of protein database search programs," Nucleic Acids Res. 25(17):3389-3402 (1997).
Arkin and Youvan, "An algorithm for protein engineering: simulations of recursive ensemble mutagenesis," Proc. Natl. Acad. Sci. 89:7811-7815 (1992).
Atherton and Sheppard, "Solid phase peptide synthesis: a practical approach," (the Practical Approach Series), Chapter 9, 107-123 (1989).
Ausubel et al., "Cross-reactivity of T-cell clones specific for altered peptide ligands of myelin basic protein," Cell Immunology 193(1): 99-107 (1999).
Ausubel et al., "Current Protocols in Molecular Biology," John Wiley & Sons Inc., Unit 19.3, 29 pages (1999).
Bird et al., "Single-chain antigen-binding proteins," Science 242(4877):423-426 (1988).
Carter et al., "Humanized of an anti-p185HER2 antibody for human cancer therapy," Proc. Natl. Acad. Sci. USA 89(10): 4285-4289 (1992).
Carter et al., "High level *Escherichia coli* expression and production of a bivalent humanized antibody fragment," Biotechnology 10(2): 163-167 (1992).
Certified English language translation of JP 2008-001610, "Separation of target protein or protein particles for detection and its operation," 12 pages.
Chen et al., "Electron tomography reveals polyhedrin binding and existence of both empty and full cytoplasmic polyhedrosis virus particles inside infectious polyhedra," J. Virol. 85(12): 6077-6081 (2011).
Chiu E, "Insect Virus polyhedra, infectious protein crystals that contain virus particles," Curr Opin. Struct. Biol. 22(2); 234-240 (2012).
Clackson et al., "Making antibody fragments using phage display libraries," Nature 352(6336):624-628 (1991).
Coulibaly et al., "The atomic structure of baculovirus polyhedral reveals the independent emergence of infectious crystals in DNA and RNA viruses," Proc. Natl. Acad. Sci. USA 106(52): 22205-22210 (2009).
Coulibaly et al., "The molecular organization of cypovirus polyhedra," Nature 446(7131): 97-101.
Dale et al., "Evaluation in macaques of HIV-1 DNA vaccines containing primate CpG motifs and fowlpoxvirus vaccines co-expressing IFNgamma or IL-12," Vaccine 23(2):188-197 (2004).
Dayhoff et al., "A model of evolutionary change in proteins," in Atlas of Protein Sequence and Structure, vol. 5, Supp. 3, The National Biomedical Research Foundation, Silver Spring, MD, pp. 345-352 (1979).
Delagrave et al., "Recursive ensemble mutagenesis," Protein Eng. 6(3): 327-331 (1993).
Derwent English Abstract for Japanese Patent Publication JP 2006-170486, published Jan. 1, 2008, entitled "Element for protein isolation or detection, consists of carrier protein particles containing target protein in sample used as isolation source, and specific protein with interaction property," Derwent Accession No. 17301689, 2 pages.
Devereux et al., "A comprehensive set of sequence analysis programs for the VAX," Nucleic Acid Research 12(1): 387-395 (1984).
Faustin et al., "Reconstituted NALP1 Inflammasome Reveals Two-Step Mechanism of Caspase-1 Activation." Molecular Cell 25:713-724 (2007).
Gonnet et al., "Exhaustive matching of the entire protein sequence database," Science 256(5062): 1443-1445 (1992).
Hornung et al., "Silica crystals and aluminum salts mediate NALP-3 inflammasome activation via phagosomal destabilization," Nat. Immunol. 9(8): 847-856 (2008).
Huston et al., "Protein engineering of antibody binding sites: recovery of specific activity in an anti-digoxin single-chain Fv analogue produced in *Escherichia coli*," Proc. Natl. Acad. Sci. USA 85(16): 5879-5883 (1988).

(56) References Cited

OTHER PUBLICATIONS

Ijiri et al., "Structure-based targeting of bioactive proteins into cypovirus polyhedral and application to immobilized cytokines for mammalian cell culture," Biomaterials 30(26): 4297-4308 (2009).
Ikeda et al., "Molecular characterization of Bombyx mori cytoplasmic polyhedrosis virus genome segment 4," J. Virol. 75(2): 988-995 (2001).
Ikeda et al., "Immobilization of diverse foreign proteins in viral polyhedral and potential application for protein microarrays," Proteomics 6(1):54-66 (2006).
Ji et al., "How baculovirus polyhedra fit square pegs into round holes to robustly package viruses," EMBO J. 29(2):505-514,2010).
Jones et al., "Replacing the complementarity-determining regions in a human antibody with those from a mouse," Nature 321(6069): 522-525 (986).
Kelleher et al., "A randomized, placebo-controlled phase 1 trial of DNA prime, recombinant fowlpox virus boost prophylactic vaccine for HIV-1," AIDS 20(2):294-297 (2006).
Keoshkerian et al., "Effector HIV-specific cytotoxic t-lymphocyte activity in long-term nonprogressors: associations with viral replication and progression," J Med Virol 71(4): 483-491 (2003).
Kohler and Milstein, "Continuous culture of fused cells secreting antibody of predefined specificity," Nature 256: 495-499 (975).
Kortt et al., "Single-chain Fv fragments of anti-neuraminidase antibody NC10 containing five- and ten- residue linkers form dimers and with zero-residue linker a trimer," Protein Engineering 10(4): 423-433 (1997).
Kunkel et al., "Rapid and efficient site-specific mutagenesis without phenotypic selection," Methods in Enzymol., 154: 367-382 (1987).
Kunkel T., "Rapid and efficient site-specific mutagenesis without phenotypic selection," Proc. Natl. Acad. Sci. 82: 488-492 (1985).
Larrick et al., "Polymerase chain reaction using mixed primers: cloning of human monoclonal antibody variable region genes from single hybridoma cells," Biotechnology 7:934-938 (1989).
Liu et al., "Chimeric mouse-human IgG1 antibody that can mediate lysis of cancer cells," Proc. Natl. Acad. Sci. 84: 3439-3443 (1987).
Marks et al., "By-passing immunization. Human antibodies from V-gene libraries displayed on phage," J. Mol. Biol. 222(3): 581-597 (1991).
MicroCube Technology Vaccine Platform—collaboration with Monash University, Burnet Institute website [online] [retrieved on Feb. 5, 2014] Retrieved from:<URL:burnet.edu.au/projects/8_microcube_technology_vaccine_platform_collaboration_with_monash_university, 4 pages.
MicroCube Technology Vaccine Platform brochure, Published Jul. 2011 [online] [Retrieved on Feb. 5, 2014] from:<URL:monash.edu.au/assets/pdf/industry/microcube-info.pdf, 2 pages.
Mori et al., "Immobilization of bioactive fibroblast growth factor-2 into cubic proteinous microcrystals (bombyx mori cypovirus polyhedera) that are insoluble in a physiological cellular environment," J. Biol. Chem. 282(23): 17289-17296 (2007).
Mori et al., "Expression of Bombyx mori cytoplasmic polyhedrosis virus polyhedrin in insect cells by using a baculovirus expression vector, and its assembly into polyhedra," J. Gen. Virol. 74(1): 99-102 (1993).
Morrison et al., "Chimeric human antibody molecules: mouse antigen-binding domains with human constant region domains," Proc. Natl. Acad. Sci. U.S.A. 81(21): 6851-6855 (1984).
Ohtsuka et al., "Mutations of cypovirus polyhedrin and applications of polyhedra to protein nanocontainers," Nanotech Conference & Expo 2010, NSTI, USA [abstract] (2010), retrieved from:<http://www.nsti.org/procs/Nanotech2010v3/4/T30.811, 1 page.
Padlan, E.A., "A Possible procedure for reducing the immunogenicity of antibody variable domains while preserving their ligand-binding properties," Mol. Immunol. 28(4-5): 489-498.
Pedersen et al., "Comparison of surface accessible residues in human and murine immunoglobulin Fv domains. Implication for humanization of murine antibodies," J. Mol. Biol. 235(3): 959-973 (1994).
Presta et al., "Antibody engineering," Curr. Opin. Biotechnol. 3(4): 394-398 (1992).
Reichmann et al., "Reshaping human antibodies for therapy," Nature 332(6162):323-329 (1988).
Rice-Ficht et al., "Polymeric particles in vaccine delivery," Curr. Opin. Microbiol. 13(1): 106-112 (2010).
Roberge et al., "A Strategy for a convergent synthesis of N-linked glycopeptides on a solid support," Science 269(5221): 202-204 (1995).
Sambrook et al., "Molecular Cloning: A Laboratory Manual," Second Edition, Cold Spring Harbor Laboratory, Cold Spring Harbor, N.Y. Sections 1.101 to 1.104, 16 and 17 (1989).
The Structural Virology Laboratory website at Monash University, Last updated Jul. 25, 2012 [online] [retrieved on Feb. 5, 2014] Retrieved from:<URL:med.monash.edu.au/biochem/staff/coulibaly.html, 4 pages.
Thomson et al., "Development of a synthetic consensus sequence scrambled antigen HIV-1 vaccine designed for global use," Vaccine 23(38): 4647-4657 (2005).
Tomizuka et al., "Double-trans-chromosomic mice: maintenance of two individual human chromosome fragments containing Ig heavy and κ loci and expression of fully human antibodies," Proc. Natl. Acad. Sci. U.S.A. 97(2): 722-727 (2000).
Ward et al., "Binding activities of a repertoire of single immunoglobulin variable domains secreted from *Escherichia coli*," Nature 341(6242): 544-546 (1989).
Winter et al., "Humanized antibodies," Trends Pharmacol. Sci 14(5):139-143 (1993).
Xia et al., "Structural Comparisons of Empty and Full Cytoplasmic Polyhedrosis Virus," J. Biol. Chem. 278(2):1094-1100 (2003).
Yu et al., "3.88 Å structure of cytoplasmic polyhedrosis virus by cryo-electron microscopy," Nature 453(7193): 415-419 (2008).
International Search Report, dated Aug. 17, 2011, in connection with corresponding International Application No. PCT/AU2011/000763, 4 pages.
Written Opinion, dated Aug. 17, 2011, in connection with corresponding International Patent Application No. PCT/AU2011/000763, 5 pages.
International Preliminary Report on Patentability, dated Dec. 28, 2012, in connection with corresponding International Patent Application No. PCT/AU2011/00076, 6 pages.
Rule 161(2) and 162 Communication, dated Feb. 27, 2013, in connection with corresponding European Patent Application No. 11797391.7, 2 pages.
Response, submitted Sep. 9, 2013, to Rule 161(2) and 162 Communication, dated Feb. 27, 2013, in connection with corresponding European Patent Application No. 11797391.7, 3 pages.
Extended European Search Report and Search Opinion, dated Dec. 18, 2013, in connection with European Patent Application No. 11797391.7, 5 pages.
Office Action, dated Aug. 29, 2014, in connection with U.S. Appl. No. 13/806,117, 16 pages.
Response, filed Nov. 7, 2014, to Extended European Search Report and Search Opinion, dated Dec. 18, 2013, in connection with European Patent Application No. 11797391.7, 8 pages.
Response, submitted Feb. 27, 2015, to Office Action, dated Aug. 29, 2014, in connection with U.S. Appl. No. 13/806,117, 24 pages.
Office Action, dated May 19, 2015, in connection with Japanese Patent Application No. 2013-515635 [Original document in Japanese and English language translation], 6 pages.
Office Action, dated Jul. 24, 2015, in connection with U.S. Appl. No. 13/806,117, 31 pages.
Response filed Oct. 23, 2015, to Office Action, dated Jul. 24, 2015, in connection with U.S. Appl. No. 13/806,117, 80 pages.
Communication pursuant to Article 94(3) EPC, dated Jan. 25, 2016, in connection with European Patent Application No. 11797391.7, 4 pages.
Final Office Action, dated Feb. 9, 2016, in connection with U.S. Appl. No. 13/806,117, 43 pages.
Office Action, dated Apr. 12, 2016, in connection with Japanese Patent Application No. 2013-515635 [English translation], 2 pages.

(56) References Cited

OTHER PUBLICATIONS

Response, filed Jul. 8, 2016, to Article 94(3) EPC, dated Jan. 25, 2016, in connection with European Patent Application No. 11797391.7, 29 pages.
Communication under Rule 71(3) EPC (Intention to Grant), dated Sep. 13, 2016, in connection with European Patent Application No. 11797391.7, 77 pages.
Letter/Written Disclosure of the Supplemental Information Disclosure Statement for the above-refereneed agplication, filed herewith on Oct. 8, 2018, 2 pages.
Anduleit et al., "Crystal lattice as biological phenotype for insect viruses," Protein Science 14:2741-2743 (2005).
Lu et al., "Persistently Active Microbial Molecules Prolong Innate Immune Tolerance In Vivo," PLoS Pathog. 9(5):e1003339 (2013).
Matsumoto et al., "Bone regeneration by polyhedral microcrystals from silkworm virus," Scientific Reports 2:935 (2012).
McLinden et al., "Expression of foreign epitopes on recombinant occlusion bodies of baculoviruses," Vaccine 10(4):231-237 (1992).
U.S. Appl. No. 14/777,457, filed Sep. 15, 2015, US 2016-0030552 A1, Feb. 4, 2016.
U.S. Appl. No. 13/989,598, filed Aug. 12, 2013, US 2013-0323282 A1, Dec. 5, 2013.
Matsushima, K., et al., Secreted Frizzled Related Protein 4 Reduces Fibrosis Scar Size and Ameliorates Cardiac Function After Ischemic Injury, Tissue Engineering: Part A, 2010, 16, 3329-3341 Published online ahead of editing on Jun. 9, 2010.†
Ji, X., et al., How baculovirus polyhedra fit square pegs into round holes to robustly package viruses, EMBO, 2010, 29, 505-514Published online ahead of print Dec. 3, 2009.†

\* cited by examiner
† cited by third party

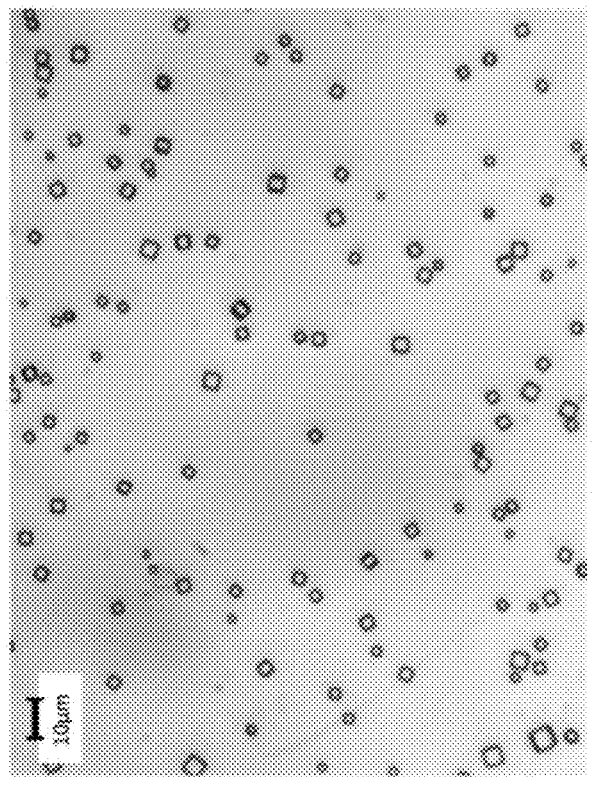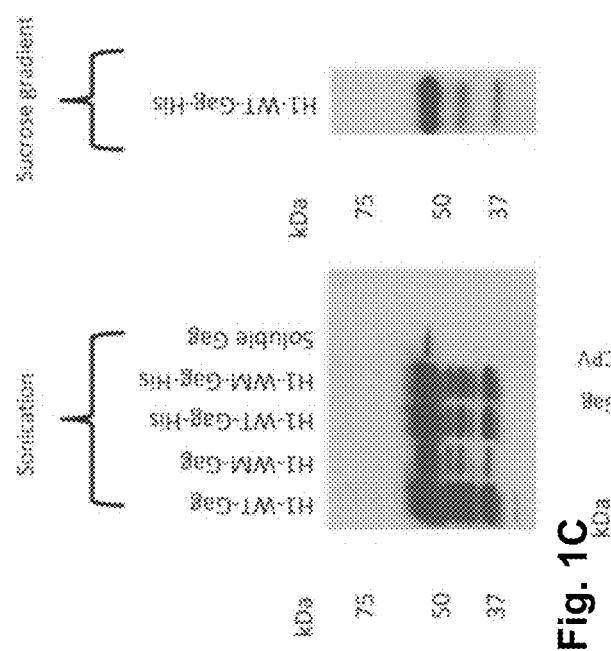

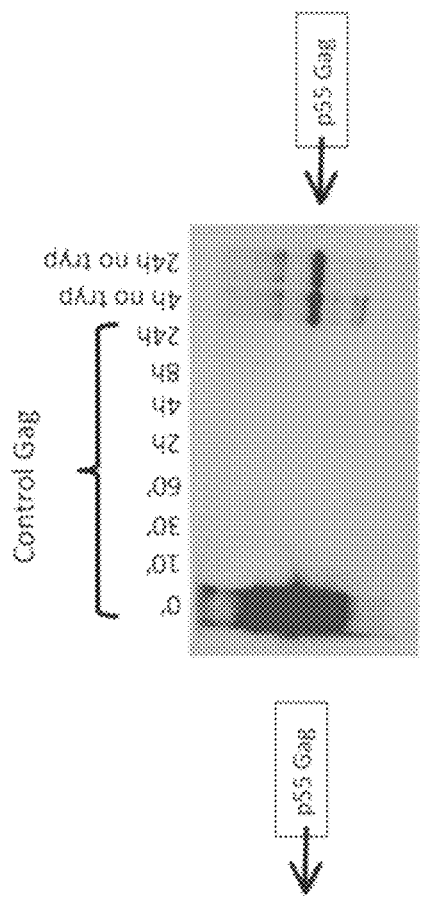
Fig. 2B
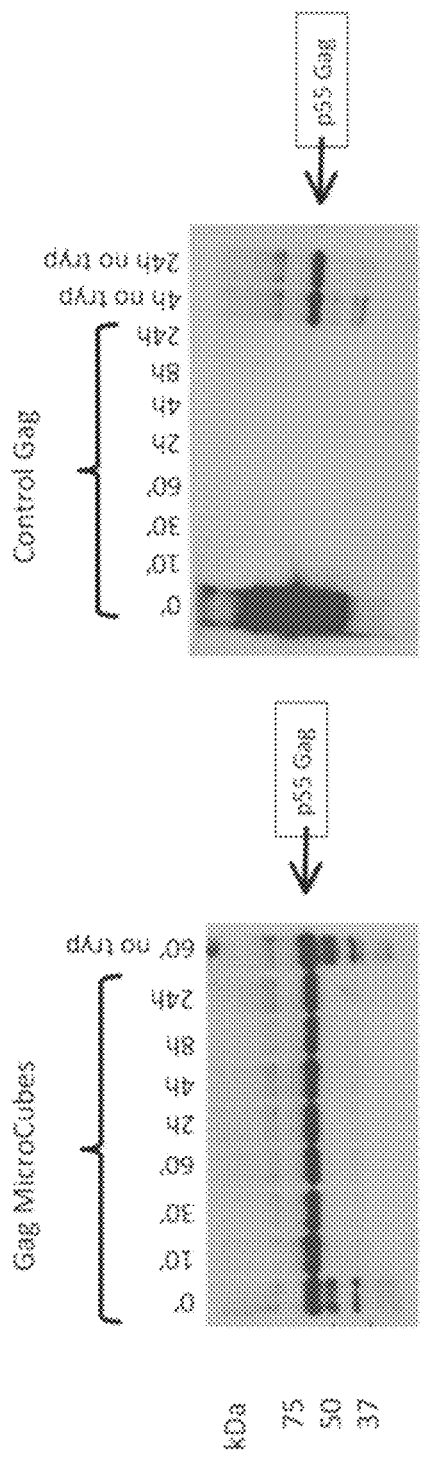
Fig. 2A
Fig. 2C

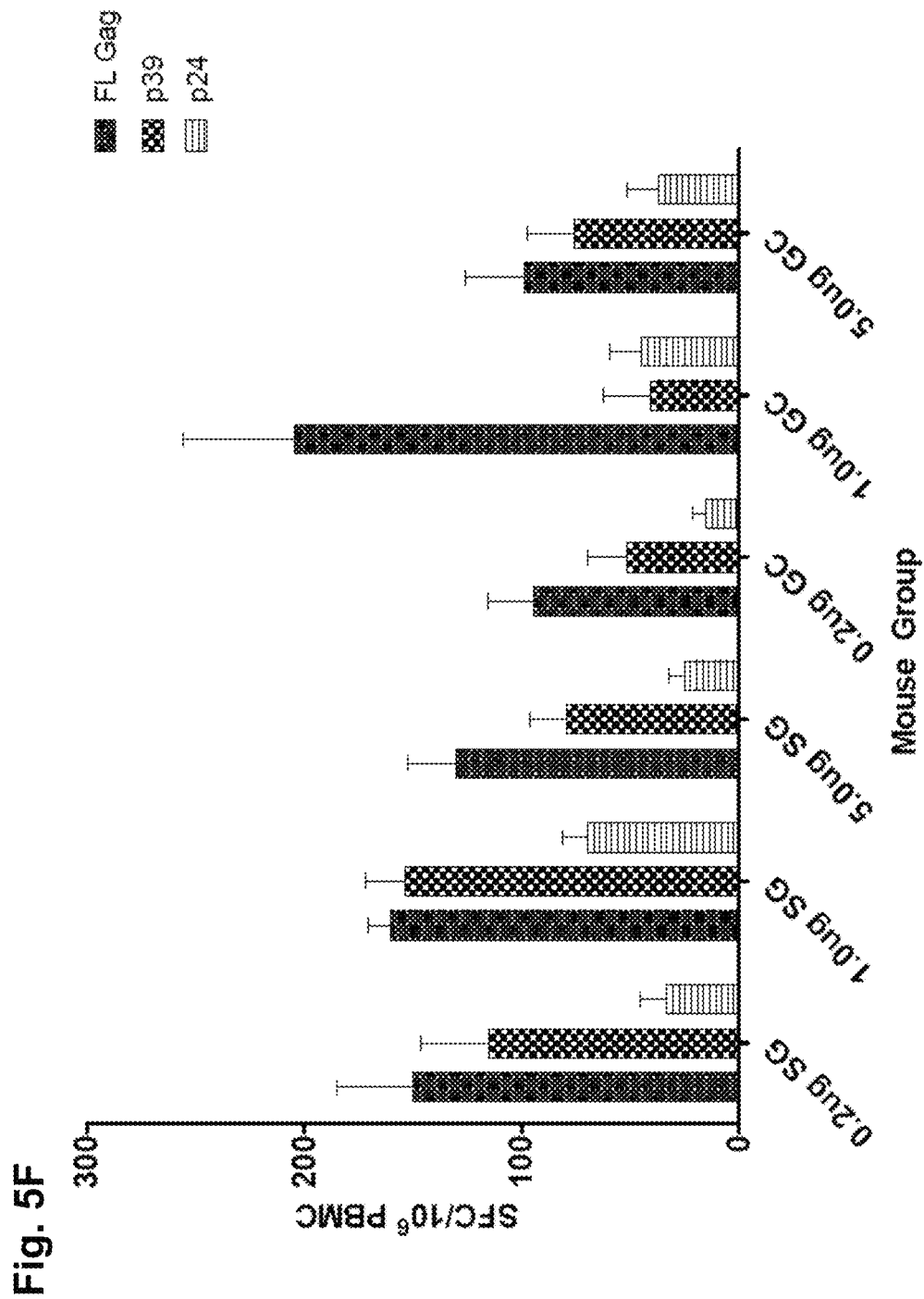

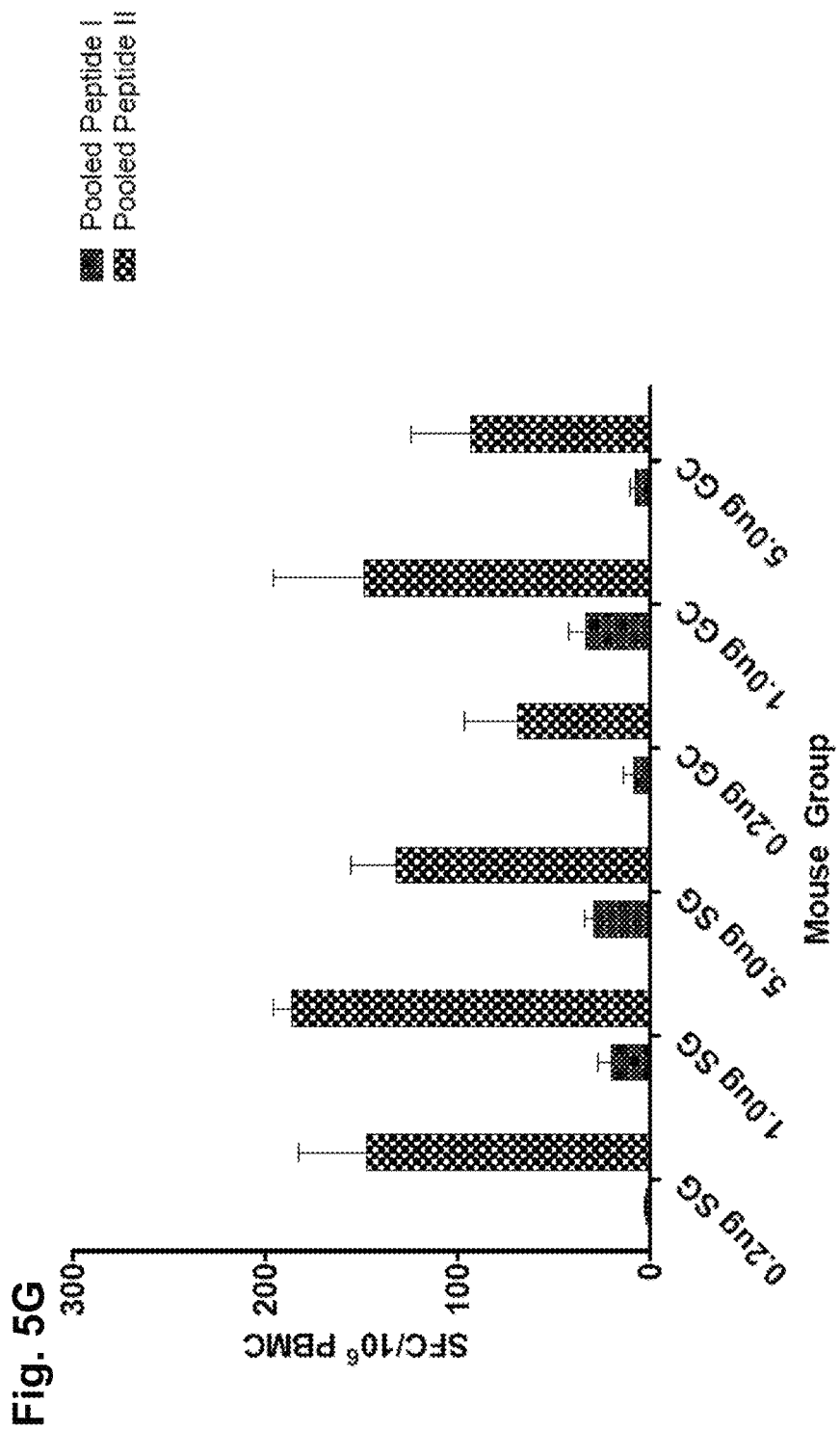

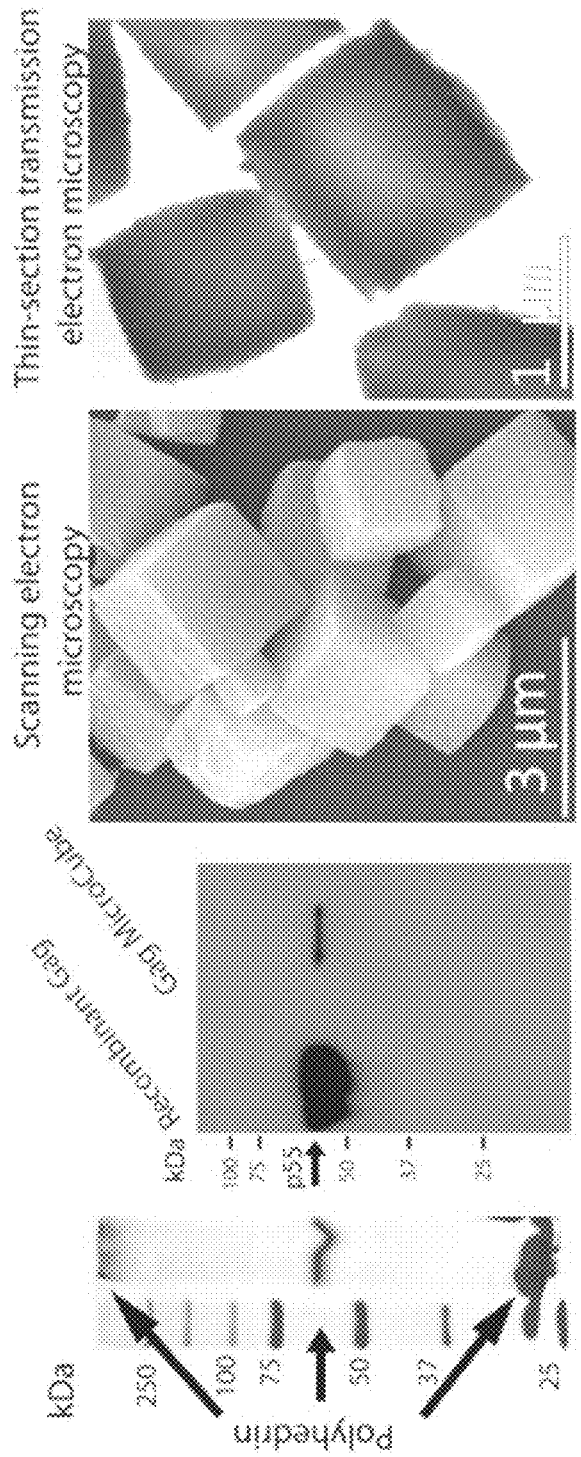

CONSTRAINED IMMUNOGENIC COMPOSITIONS AND USES THEREFOR

RELATED APPLICATIONS

This application is a divisional of co-pending patent application Ser. No. 13/806,117, filed on Dec. 20, 2012, which is the U.S. National Stage of International Application. No. PCT/AU2011/000763, filed 23 Jun. 2011, titled "CONSTRAINED IMMUNOGENIC COMPOSITIONS AND USES THEREFOR," which claims benefit of priority to U.S. Provisional Patent Application Ser. No. 61/357,667, filed 23 Jun. 2010. The subject matter of each of the above-referenced applications is incorporated by reference in its entirety.

FIELD

The present invention relates to immunogenic, proteinaceous, constrained complexes and to compositions and kits comprising them. In some embodiments, the invention relates to delivery of constrained antigens to subjects to induce an immune response.

BACKGROUND

Bibliographic details of references in the subject specification are also listed at the end of the specification.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Despite much progress in understanding the mechanisms of immunity, vaccines against major pathogens such as HIV and *Plasmodium* spp. remain elusive. In recent years, alternative antigen delivery systems have been actively investigated for greater efficacy, safety and ease of production. The most successful of these approaches has been virus-like particles (VLP) relying on self-assembly of viral structural proteins (HBV, papillomavirus). However, many pathogens do not produce such assemblies and there are limitations to the size of the antigens that can be incorporated into VLP scaffolds. The administration of antigens as particles is thought to have a number of advantages. Antigen presenting cells take up particulate antigens preferentially and traffic them to cellular compartments facilitating the production of antibody and cellular responses (see review by Rice-Ficht et al., *Current Opinion in Microbiology*, 13: 106-112, 2010).

There is a need for a versatile platform technology able to present antigens of various nature and size and induce robust humoral and cellular responses.

SUMMARY

Each embodiment in this specification is to be applied mutatis mutandis to every other embodiment unless expressly stated otherwise.

The articles "a" and "an" are used herein to refer to one or to more than one (i.e. to at least one) of the grammatical object of the article. By way of example, "a cell" means one cell or more than one cell. An "antigen" means one antigen or more than one antigen.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The present invention relates broadly to the use of elements of insect virus crystals, referred to as polyhedra, to present antigens associated with pathogens, diseases or conditions affecting human or non-human mammalian subjects and to induce immune responses. The ability of antigen-polyhedrin complexes in the form of polyhedra (herein also referred to as MicroCubes) to elicit an immune response is surprising as it was assumed that the crystals would be rapidly cleared from the organism, or be toxic, or be unable to be processed by antigen presenting cells, or be capable of eliciting only either a humoral or a cellular immune response.

In some embodiments, polyhedral polyhedrin and a polypeptide comprising an antigen form a stable complex which at least partially constrains the structure of the antigen and/or protects the antigen from degradation. Thus, in some embodiments, the present invention provides a vehicle for presenting antigens of interest to the immune system. In nature, viral polyhedra contain multiple viral particles embedded (occluded) within the crystalline lattice which acts as a survival and transmission mechanism. The encapsulated viral particles can remain infectious in soil for many years and the life cycle is continued when an insect ingests the crystals that break down in the alkaline mid-gut to release infective viral particles. As known in the art, polyhedrin targeting peptides (tags) can be used to draw fusion proteins comprising them into a crystal structure comprising polyhedrin.

The term "complex" refers to the "antigen-polyhedrin subunit" which forms the modified CPV polyhedrin as well as the "modified polyhedra". In some preferred embodiments, the term "complex" refers to the modified polyhedra (the terms "MicroCubes", "polyhedra crystals", "modified polyhedra crystals", "polyhedra", "polyhedrin" or "micromolecular structure" and the like are used interchangeably) comprising the antigen of a pathogen or disease or condition affecting a human or non-human mammalian subject.

In some embodiments, the present invention employs protocols developed previously to express polypeptides as fusion proteins in insect polyhedra. This technology is known in the art and may be reviewed for example in Ikeda et al., *J. Virol.* 75: 988-995, 2001; Ikeda et al., *Proteomics*, 6: 54-66, 2006; Mori et al., *J. Biol. Chem.* 282(23): 17289-17296, 2007; Ijiri et al. *Biomaterials* 30: 4297-4308, 2009 incorporated herein in their entirely by reference. The present invention is not limited to a particular method of production as such may vary.

The present invention provides an immunogenic or vaccine composition comprising a complex comprising an antigen of a pathogen or other antigen against which a immune response is sought in a human or non-human animal subject and a polyhedrin or polyhedrin-like protein.

"Polyhedrin" and "polyhedrin-like" encompasses any naturally occurring form of polyhedrin from any cytoplasmic polyhedrosis virus (cypo) (CPV) as well as their biologically active portions and variants, analogs, homologs or derivatives of these, as defined herein. Different polyhedrin polypeptide and peptide sequences are available in the art (see NCBI Entrez Search). A polyhedrin may be selected from the art and routinely tested in the methods described herein. Polyhedrin molecules produced by CPV are distinct from those produced by baculoviruses. They differ in structure and the viruses are unrelated. Differences are described between their molecular structures in Coulibaly et al., *Proc. Natl. Acad. Sci. U.S.A.* 106(52): 22205-22210, 2009—baculovirus polyhedra have an envelope that may prevent full access to antigens their cellular localisation is distinct as CPVs replicate in the cytoplasm and baculoviruses in the nucleus.

In some embodiments, the MicroCubes are in isolated, homogeneous, fully or partly purified form. Isolation and/or purification can be carried out by methods known in the art including salt fractionation, ion exchange chromatography, gel filtration, size-exclusion chromatography, size-fractionation, and affinity and immunoaffinity chromatography. FACS separation may also be employed.

The term "isolated" or "purified" means material that is substantially or essentially free from components that normally accompany it in its native state. For example, an "isolated complex", as used herein refers to a complex isolated from the cellular, cell-free, or molecular mixtures used in its production. In some embodiments, the purified complex is at least 95 to 99% pure.

As noted, in one preferred embodiment, the polyhedrin is derived from a cytoplasmic polyhedrosis (cypo) virus (CPV). In another embodiment, the polyhedrin is not derived from a baculovirus.

In an illustrative embodiment, delivery of the complex to a subject in substantially particulate polyhedral form induces an immune response thereto. In accordance with the present invention, the polyhedron reduces degradation of antigens. In some embodiments, it also activates the immune response and therefore potentially enhances the antigen-specific immune response.

In an illustrative example, an antigen against which an immune response is sought is an antigen associated with a condition such as a tumor i.e., a tumor antigen. Accordingly, in some embodiments, the invention employs one or more antigens that are described in the art as candidate antigens for vaccination purposes because, for example, they engender an effective immune response in an animal model, and re-package the antigen(s) as a complex with polyhedrin that forms micromolecular polyhedra wherein the antigen is structurally and physically constrained. Without being bound by any particular theory or mode of action, it is proposed that delivery of antigen in particulate polyhedral form will induce enhanced cellular and/or immune responses, preferably both. Alternatively, or in addition, slow or sustained release of antigen from the micromolecular structure is proposed to reduce the need for multiple administrations and/or generate higher titre/strength cellular or antibody responses.

In one embodiment the invention provides a stable immunogenic or vaccine composition comprising a complex comprising an antigen of a pathogen or other antigen against which a immune response is sought in a human or non-human animal subject and a polyhedrin protein derived from a cytoplasmic polyhedrosis virus (CPV) wherein delivery of the complex to a subject in substantially particulate polyhedral form induces an immune response thereto.

Reference to "stable" includes that the antigen component of the complex in the polyhedron is substantially resistant to degradation under physiological or environmental conditions or exhibits decreased degradation compared to a control such as the antigen in the absence of the complex or polyhedra comprising same.

In some embodiments, the antigen in the polyhedra is heat stable. For example, as described in the Examples, MicroCube antigens are stable at between about 4° C. and about 21° C. and even at about 37° C. In some other embodiments, the antigen in the polyhedra displays decreased degradation.

In some embodiments, reference to "decreased degradation" refers to a composition displaying less than 50%, or less than 40%, less than 30%, less than 20%, less than 10%, less than 1% antigen degradation over a storage period under conditions wherein the same antigen not present in a complex with polyhedrin or in a polyhedron exhibits more than 50%, 60%, 70% or more antigen degradation. In some embodiments, the antigen in the polyhedron is resistant to enzymatic such as trypsin degradation.

In an illustrative non-limiting embodiment, the polyhedrin is derived from *Bombyx mori* CPV. In some embodiments, the enzyme is trypsin.

By "derived from" is meant naturally occurring forms and functional variants of naturally occurring forms and therefore includes sequences directly or indirectly derived from an organism. For example, a viral polypeptide such as polyhedrin is "derived from" a particular polypeptide of a virus (viral polypeptide) if it is (i) encoded by an open reading frame of a polynucleotide of that virus (viral polynucleotide), or (ii) displays sequence and or structure-functional similarity to polypeptides of that virus as described herein. Functional variants are described herein and include derivatives which may be fragments of a polyhedrin polypeptide.

In some embodiments, the antigen is fused to a polyhedrin targeting peptide such as the targeting peptide is derived from the N-terminal H1 α-helix or VP3 polyhedrin recognition signal of polyhedrin of CPV or is a functional variant thereof. In some embodiments, the targeting peptide is derived from the N-terminal H1 α-helix or VP3 polyhedrin recognition signal of polyhedrin of *Bombyx mori* CPV or is a functional variant thereof.

For the avoidance of doubt in some embodiments antigen-polyhedrin targeting fusion proteins are chimeric polypeptides by which is meant that the combination does not occur in nature and that the protein comprises an antigen from one organism and polyhedrin targeting peptide derived from a second organism, such as different species.

In an illustrative embodiment, a chimeric antigen-polyhedrin targeting protein of the present invention is produced wherein at least two polypeptides or peptides derived from different species are linked by covalent bonds, either by being expressed as part of the same expression product or by synthesis. In both cases the resulting polypeptide may be referred to as a fusion protein. Direct attachment of antigen to polyhedra by covalent cross-linking or coating is also contemplated.

The terms "polypeptide" "protein" and "peptide" and "glycoprotein" are used interchangeably and mean a polymer of amino acids not limited to any particular length. The term does not exclude modifications such as myristylation, glycosylation, phosphorylation and addition and/or deletion of signal sequences.

A "part" or "portion" or "region" or "domain" of a polypeptide such as a polyhedrin H1 α-helix (tag) of cypovirus is defined as having a minimal size of at least about 10 amino acids or about 20 to 30 amino acids, 15 to 100 amino acids or about 5 to 80 amino acids or about 15 to 120 amino acids.

As used herein, an "immune response" refers to the reaction of the body as a whole to the presence of a composition of the present invention which includes making antibodies and developing immunity to the composition. Immunity may develop as a result of activation of both innate and adaptive arms of the immune response. Therefore, an immune response to an antigen of a pathogen of a human or non-human animal or an antigen associated with a human condition (such as cancer) or disease as described herein also includes the development in a subject of a humoral and/or cellular immune response to the antigen of interest. Any such response can be modified, including enhanced or activated, by stimulation of an innate immune response. A "humoral immune response" is mediated by antibodies produced by plasma cells. A "cellular immune response" is one mediated by T lymphocytes and/or other white blood cells. An "immunological response" or "immune response" to an antigen includes the development in a subject of a humoral (B-cell) and/or a cellular immune (T-cell) response to an antigen. The polyhedral component of the subject complex is not an antigen as defined herein however as determined herein it elicits an immune response including cytokine secretion and or the activation of inflammasome potentially enhancing an antigen specific immune response as sought. The ability of a particular antigen to stimulate a cell-mediated or humoral immunological response, including the production of antibodies by plasma cells and B-cells, the activation of suppressor T-cells and/or γδT cells may be determined by any number of assays, such as by lymphoproliferation (lymphocyte activation) assays, CTL cytotoxic cell assays, or by assaying for T-lymphocytes specific for the antigen in a sensitised subject. Such assays are well known in the art. Methods of measuring cell-mediated immune response include measurement of intracellular cytokines or cytokine secretion by T-cell populations, or by measurement of epitope specific T-cells. The immune response may serve to neutralise infectivity, reduce transmission or load, and/or mediate antibody-complement, or antibody dependent cell cytotoxicity (ADCC) to provide protection to an immunised host. Immune responses can be determined using standard immunoassays and neutralisation assays, as known in the art.

An "immunogenic composition" is a composition that comprises an antigenic molecule where administration of the composition to a subject results in the development in the subject of a humoral and/or a cellular immune response to the antigenic molecule of interest. In accordance with the present invention, the polyhedrin protein or peptide is also immunogenic and stimulates an immune response suitable for enhancing the immune response to the antigen against which an immune response is sought.

Assays for assessing an immune response are described in the Examples and may comprise in vivo assays, such as assays to measure antibody responses and delayed type hypersensitivity responses. In an embodiment, the assay to measure antibody responses primarily may measure B-cell function as well as B-cell/T-cell interactions. For the antibody response assay, antibody titers in the blood may be compared following an antigenic challenge. As used herein, "antibody titers" can be defined as the highest dilution in post-immune sera that resulted in a value greater than that of pre-immune samples for each subject.

These levels can be quantitated according to the type of antibody, as for example, IgG, IgG1, IgG2, IgG3, IgG4, IgM, IgA or IgD. Also, the development of immune systems may be assessed by determining levels of antibodies and lymphocytes in the blood without antigenic stimulation.

The in vitro assays may comprise determining the ability of cells to divide, or to provide help for other cells to divide, or to release lymphokines and other factors, express markers of activation, and lyse target cells. Lymphocytes in mice and man can be compared in in vitro assays. In an embodiment, the lymphocytes from similar sources such as peripheral blood cells, splenocytes, or lymph node cells, are compared. It is possible, however, to compare lymphocytes from different sources as in the non-limiting example of peripheral blood cells in humans and splenocytes in mice. For the in vitro assay, cells may be purified (e.g., B-cells, T-cells, and macrophages) or left in their natural state (e.g., splenocytes or lymph node cells). Purification may be by any method that gives the desired results. The cells can be tested in vitro for their ability to proliferate using mitogens or specific antigens. The ability of cells to divide in the presence of specific antigens can be determined using a mixed lymphocyte reaction (MLR) assay. Supernatant from the cultured cells can be tested to quantitate the ability of the cells to secrete specific lymphokines. The cells can be removed from culture and tested for their ability to express activation antigens. This can be done by any method that is suitable as in the non-limiting example of using antibodies or ligands which bind to the activation antigen as well as probes that bind the RNA coding for the activation antigen.

In some embodiments, phenotypic cell assays can be performed to determine the frequency of certain cell types. Peripheral blood cell counts may be performed to determine the number of lymphocytes or macrophages in the blood. Antibodies can be used to screen peripheral blood lymphocytes to determine the percent of cells expressing a certain antigen as in the non-limiting example of determining CD4 cell counts and CD4/CD8 ratios.

Accordingly, the present invention provides a composition comprising a complex as herein described wherein the immune response to the complex includes a cellular and a humoral response.

In some embodiments, the immune response to the polyhedrin or polyhedrin peptide portion of the complex comprises a cellular or humoral response.

In some embodiments, the immune response to the polyhedrin or polyhedrin peptide portion of the complex comprises inflammasome activation.

In some further embodiments, the composition comprising a pharmaceutically or physiologically acceptable carrier and/or diluent.

The term "vaccine" as used herein refers to a pharmaceutical composition comprising an immunologically active component that induces an immunological response in a subject and possibly but not necessarily one or more additional components that enhance the immunological activity of said active component (for example an adjuvant). A vaccine may additionally comprise further components typical to pharmaceutical compositions. The immunologically active component of a vaccine according to the present invention comprises an antigen of a pathogen or other antigen against which a immune response is sought in a human or non-human animal subject and a polyhedrin protein. The terms "vaccine" and "vaccine composition" are used interchangeably in the present invention. As determined herein, the polyhedrin portion also induces an immune response.

"Subjects" contemplated in the present invention include any animal of commercial or humanitarian interest including conveniently, primates, livestock animals including fish, crustacea, and birds, laboratory test animals, companion animals, or captive wild animals. In some embodiments the subject is a mammalian animal. In particular embodiments, the subject is a human subject. In some embodiments, "subjects" are humans or animals including laboratory or art accepted test or vehicle animals. "Patients" include human subjects in need of treatment or prophylaxis.

In another embodiment, the invention provides an immunogenic composition comprising an antigen of a pathogen or other antigen against which an immune response is sought and a CPV polyhedron wherein delivery of the composition induces an immune response to the antigen and wherein the CPV polyhedron enhances the immune response to the antigen.

In some embodiments, the invention provides an immunogenic composition comprising CPV polyherdra for use in conjunction with an antigen to stimulate an immune response to the antigen. In some embodiments, the CPV polyhedron is derived from *Bombyx mori*.

In another embodiment, the present invention provides an immunogenic composition as described herein comprising a complex comprising an antigen of a pathogen or other antigen against which a immune response is sought in a human or non-human animal subject and a polyhedrin protein for use in the manufacture of a vaccine for the treatment or prevention of an infection, disease or condition associated with the antigen.

In another embodiment, there is provided for a use of an immunogenic composition as described herein comprising a complex comprising an antigen of a pathogen or other antigen against which a immune response is sought in a human or non-human animal subject and a polyhedrin protein in the manufacture of a medicament for the treatment or prevention of an infection, disease or condition associated with the antigen.

In another broad embodiment, there is provides a method for eliciting an immune response in a subject or patient, the method comprising administering to the subject or patient an effective amount of an immunogenic composition as described herein comprising a complex comprising an antigen of a pathogen or other antigen against which a immune response is sought in a human or non-human animal subject and a polyhedrin protein, under conditions to elicit an immune response.

Further, the invention includes method for immunising a subject against infection or disease or condition associated with the antigen comprising administering to the subject an immunogenic composition as described herein comprising a complex comprising an antigen of a pathogen or other antigen against which a immune response is sought in a human or non-human animal subject and a polyhedrin protein.

Furthermore, the present invention provides a method for treating or preventing infection by a pathogen or a disease (cancer) or other condition comprising administering to the subject an immunogenic composition as described herein comprising a complex comprising an antigen of a pathogen or other antigen against which a immune response is sought in a human or non-human animal subject and a polyhedrin protein, for a time and under conditions sufficient to treat or prevent the infection or cancer/disease or condition.

In one embodiment, the present invention provides a method for inducing an immune response in a subject, the method comprising administering to the subject an effective amount of a complex comprising (a) an antigen of a pathogen or other antigen associated with a condition against which an immune response is sought; and (b) polyhedrin, wherein administration is for a time and under conditions sufficient for the antigen to induce an immune response.

In another embodiment, the present invention provides a method for inducing an immune response in a subject, the method comprising administering to the subject an effective amount of a complex comprising (a) a chimeric fusion polypeptide comprising a polyhedrin targeting peptide and an antigen of a pathogen or other antigen associated with a condition against which an immune response is sought; and (b) polyhedrin, wherein administration is for a time and under conditions sufficient for the antigen to induce an immune response.

In a similar embodiment, the invention provides a method for treatment or prophylaxis of a viral infection in a subject comprising administering a complex comprising a virus antigen and/or fusion protein comprising same according to the present invention for a time and under conditions sufficient to treat or prevent the virus infection.

In a similar embodiment, the invention provides a method for treatment or prophylaxis of an infection in a subject comprising administering a complex comprising a pathogen antigen or a tumor/cancer antigen and/or fusion protein comprising same according to the present invention for a time and under conditions sufficient to treat or prevent the pathogen or tumor/cancer infection/condition.

In other similar embodiments, the invention provides the subject complexes and fusion proteins for use in the treatment and/or prophylaxis of a viral infection or a pathogen or tumor/Cancer infection/condition. In further similar embodiments, the complexes and/or fusion proteins are proposed for use in the manufacture of a medicament for treatment and/or prophylaxis of a viral pathogen or other pathogenic infection or tumor.

In some embodiments, the invention provides pharmaceutical compositions including immunogenic or putative vaccine compositions comprising an isolated nucleic acid molecule encoding the subject fusion polypeptide.

In some embodiments, pharmaceutical compositions including an immunogenic or putative vaccine composition are formulated with a pharmaceutically acceptable carrier and/or diluent.

In other embodiments, the present invention provides a pharmaceutical composition comprising a subject complex or fusion polypeptide as described herein.

A putative vaccine composition is one, for example, that shows promise of inducing an effective immune response in an accepted animal or cellular model.

In other embodiments, the invention provides a method for producing an isolated or purified antibody or immune cell that specifically binds to an antigen of a pathogen or other antigen against which an immune response is sought in a human or non-human animal subject or patient. The method- comprises administering to a subject an effective amount of an immunogenic composition as described herein comprising a complex comprising an antigen of a pathogen or other antigen against which a immune response is sought in a human or non-human animal subject and a polyhedrin protein, and isolating or purifying antibody or immune cells.

In some embodiments, the complex or polyhedra comprising same is in isolated, homogeneous, fully or partly purified form.

In preferred embodiments, the polyhedrin is derived from a CPV.

In further embodiments, delivery of the complex to a subject in substantially polyhedral form induces an immune response to the complex.

In some embodiments, the antigen is fused to a polyhedrin targeting peptide.

In some embodiments, the immune response to the complex includes an immune response to the polyhedrin portion of the complex and comprises a cellular or humoral immune response and/or comprises inflammasome activation. Activation may be detected by various assays such as by assaying for IL-1β secretion.

In some embodiments, the polyhedrin is not targeted to the nucleus of insect cells and does not form a polyhedral envelope.

In some embodiments, the immune response is a humoral and a cellular immune response.

The above method encompasses the production of antibodies and/or immune cells in a non-human subject. In this embodiment, antibodies, for example, are suitable for use in the manufacture of therapeutic or prophylactic antibodies. In some other embodiments, such antibodies are useful for diagnosis, screening and research. In yet another embodiment, the methods encompass the induction of a humoral and/or immune response to the antigen in a subject susceptible to the pathogen or condition or in need of treatment or prophylaxis. In the case of prophylactic or therapeutic administration, mammalian including human subjects are particularly contemplated.

In another embodiment, the present invention provides a fusion polypeptide comprising (a) a viral polyhedrin targeting peptide and (b) an antigen of a pathogen or other molecule against which an immune response is sought. In some embodiments, the fusion polypeptide is provided in a composition suitable for administration to a subject to inducing an immune response in the subject. Illustrative compositions comprise an adjuvant suitable for animal or human application as known in the art. Other illustrative compositions are formulated for delivering to mucosa such as of the nose, mouth, gut, etc.

In an illustrative embodiment, trimeric polyhedrin polypeptides are organised around a scaffold of an N-terminal helix. Polyhedra are micromolecular complexes. Trimers are organised into tetrahedral clusters of four trimers crosslinked by intermolecular disulphide bonds (Coulibaly et al., *Nature*, 446: 97-101, 2007; Coulibaly et al., 2009 (supra)). In particular embodiments, the subject polyhedra do not comprise baculovirus or cypovirus viral or viral-like particles.

In another embodiment, the present invention provides a complex comprising (a) a fusion polypeptide comprising a polyhedrin targeting peptide and an antigen of a pathogen or other antigen associated with a condition against which an immune response is sought; and (b) polyhedrin. In some embodiments, the complex is immunogenic and/or provides sustained release in a subject. In other embodiments, the complex is suitable for eliciting an enhanced immune response compared to the immune response produced by the antigen not in the form of a complex with polyhedrin nor in the form of a fusion protein with a polyhedrin targeting peptide.

In some embodiments, the complex is in the form of a recombinant or modified polyhedron comprising a plurality of fusion polypeptides comprising an antigenic portion and a polyhedrin targeting portion. In some embodiments, the antigen portion comprises one or more epitopes derived from a single pathogenic organism or condition. In other embodiments, the antigen portion comprises one or more epitopes from more than one pathogen or condition. In some embodiments, the recombinant or modified polyhedra in the size range of 0.1 um to 50 um, more particularly, 0.1 um to 10 um, depending upon the insect polyhedrin molecules employed. Particle size may be tailored to the mode of administration for immunisation.

In an illustrative embodiment, the pathogen is HIV. In a further illustrative embodiment, the antigen is HIV Gag polypeptide or an antigenic peptide thereof. As known in the art a Gag is produced as a precursor comprising a myristylated protein (p55), which is typically processed to varying degrees by proteases to form matrix protein (MA-p17), core antigen capsid protein (CA-p24), nucleo-capsid protein (NC-p7), p6, p2 and p1. HIV Gag p39 comprises p24, p9 and p6.

In another embodiment, the invention provides a method for producing a complex comprising (a) a fusion polypeptide comprising a polyhedrin targeting peptide and an antigen of a pathogen or other antigen associated with a condition against which an immune response is sought; and (b) polyhedrin, the method comprising expressing a nucleic acid molecule encoding the antigen as a fusion polypeptide with a polyhedrin targeting peptide and expressing a nucleic acid molecule encoding a polyhedrin or polyhedrin-like polypeptide in an insect or other suitable host cell and contacting the polyhedrin and fusion polypeptides for a time and under conditions sufficient for the fusion protein comprising the antigen and the polyhedrin to form a complex. In some embodiments, the two proteins are co-produced in an insect or other equivalent host cell. The complex typically comprises a plurality of copies of the fusion protein. In particular embodiments, the method further comprised isolating or purifying the complex from other cellular or culture material.

In other embodiments fusion polypeptides may be directly synthesised and combined with polyhedrin in host cells or under cell free conditions that allow the formation of polyhedrin-antigen complexes and folding and production of polyhedra or polyhedra-like particles.

In some embodiments, the methods increase the half-life or shelf life (stability) of an antigen prepared according to the above method or a composition comprising same. In some embodiments, the methods increase the resistance of the antigen preparation to enzymatic degradation or degradation under certain physiological or environmental conditions.

In some embodiments, kits such as immunodiagnostic or immunoscreening kits comprising the isolated or purified complexes or fusion proteins and/or antibodies thereto are contemplated.

In some embodiments, antibodies are produced according to a method comprising administering to a non human subject an effective amount of a complex comprising (a) a fusion polypeptide comprising a polyhedrin targeting peptide and an antigen of a pathogen or other antigen associated with a condition against which an antibody is sought; and (b) polyhedrin, wherein administration is for a time and under conditions sufficient for the antigen to induce an antibody response. In other embodiments, the fusion polypeptide is administered.

In some embodiments, antibodies are used in the manufacture of a chimeric, deimmunised, humanised or human antibodies as known in the art.

In another embodiment, the present invention contemplates methods for screening putative interacting (binding) agents for those that bind to a subject antigen in the form of a complex comprising polyhedrin or a fusion polypeptide as described herein. In some embodiments, the methods comprise contacting a purified complex or fusion protein of the present invention with a putative interacting agent and determining binding relative to controls. In some embodiments, binding agents are further tested for their ability to reduce the level or activity of a pathogen or cancerous cell from which the antigen is derived.

Further embodiments are directed to a nucleic acid molecule encoding the fusion polypeptides described herein, host cells comprising the subject complexes or fusion polypeptides, and compositions comprising purified recombinant or modified polyhedra. Compositions may include agents to facilitate destabilisation (such as pH modifiers) or stabilisation (such as cross-linking) of the complex in vivo.

Pharmaceutical compositions comprising the subject polyhedrin-antigen complexes or polyhedrin targeting peptide-antigen fusion polypeptides, or an antibody determined thereby that specifically recognises the antigen are provided.

The above summary is not and should not be seen in any way as an exhaustive recitation of all embodiments of the present invention.

BRIEF DESCRIPTION OF THE FIGURES

Some figures contain colour representations or entities. Coloured versions of the figures are available from the Patentee upon request or from an appropriate Patent Office. A fee may be imposed if obtained from a Patent Office.

FIGS. 1A-1D are photographic representations of data showing immobilization of Gag MicroCubes.

FIGS. 2A-2C are photographic representations of data showing that Gag MicroCubes are highly stable in the presence of trypsin.

FIGS. 5A-5G are graphical representations of data showing IFN-γ responses to full length HIV Gag, p39 and p24 peptides of HIV Gag.

FIGS. 9A-9D are photographic representations of data showing efficient production of antigen-polyhedra (Microcubes). FIG. 9A: SDS-PAGE analysis of 100 µg of MicroCubes. The crystals are purified to homogeneity: all three visible bands were confirmed to be the polyhedrin protein by mass spectrometry. FIG. 9B: Western Blot analysis of E. coli-produced recombinant Gag and Gag MicroCubes showing successful incorporation. FIGS. 9C and 9D: The incorporation of antigen does not disrupt the crystalline matrix of the MicroCube.

FIGS. 10A and 10B are photographic representations of bright field and fluorescent microscopy of MicroCubes containing both HIV-1 Gag and EGFP. FIG. 10C is a graphical representation of quantification of dual-incorporation by FACS. 42% of MicroCubes contain both HIV-1 Gag and EGFP.

FIG. 11A: ELISA of sera from mice (n-8) immunized with 5 µg of soluble Gag or Gag MicroCube at week 0, 7 and 10. The coating antigen is soluble Gag. FIG. 11B: IL-2 and IFN-γ ELISPOT responses of splenocytes from mice (n-8) immunized with 1 µg of soluble Gag or Gag MicroCube. $5 \times 10^5$ splenocytes were stimulated with p55, p39, p24, pooled peptides I and II, MicroCubes and Gag-MicroCubes as noted in the inset. Media alone was used as negative control and Con A as positive control (not shown). Values above the dotted line (50 SFC/$10^6$ cells) are significantly higher than the background.

FIG. 12A: Soluble Gag and Gag MicroCubes were incubated at 21° C. for 0-11 weeks. Western blot analysis revealed degradation of soluble Gag between weeks 3 and 11 while no significant degradation of Gag MicroCubes is observed. FIG. 12B: Western blot of Gag MicroCubes incubated for 2 weeks at 37° C. in human serum. FIGS. 12C and 12D: Western blot analysis of soluble Gag and Gag MicroCubes incubated with 10 µg/mL of trypsin.

FIG. 13A: Western blot analysis of Gag MicroCubes incubated at various temperatures for one week and with (TT) or without (No TT) trypsin at 37° C. for 1 hour before injection. TT samples contain slightly more Gag due to our overestimation of the amount of Gag lost by trypsin digestion. FIG. 13B Corresponding IFN-γ and IL-2 ELISPOT. Values above the dotted line (50 SFC/$10^6$ cells) are significantly higher than the background.

FIG. 15A: Human PBMCs $10^6$/ml were primed with LPS (100 pg/ml) or left untreated for 3 hours and subsequently stimulated with MicroCubes (Bm-CPV). After 6 hours, supernatants were assessed for IL-1β production by ELISA. FIG. 15B: Primed PBMCs were stimulated with MicroCubes (Bm-CPV), Alum, Silica crystals, or Nigericin. 6 h after stimulation, supernatants were analyzed for IL-1β by ELISA. FIG. 15C: Primed PBMCs were treated with the phagocytosis inhibitor latrunculin A in ascending doses and subsequently stimulated with MicroCubes (Bm-CPV), Nigericin or Alum. IL-1β release was measured by ELISA 6 hours after stimulation. FIG. 15D: Human LPS-primed PBMCs were stimulated with MicroCubes (Bm-CPV) in the presence or absence of the caspase-1 inhibitor z-YVAD (10 µM). After 6 hours, supernatants were assessed for IL-1β by ELISA. All data is from four independent donors.

FIGS. 16A and 16B are graphical representations of data showing MicroCube-mediated release of matured IL-1β is mediated by the NALP3 inflammasome. FIG. 16A: Immortalized Bone marrow-derived macrophages of wild-type mice were primed with LPS (100 ng/ml) for 3 h and subsequently stimulated with descending amounts of MicroCubes (Bm-CPV) or Nigericin. 6 h after stimulation, supernatants were analyzed for IL-1β by ELISA (supernatants). FIG. 16B: Immortalized WT, ASC-deficient or NALP3-deficient BMMs were primed for 3 hours with LPS and subsequently stimulated with descending concentrations of MicroCubes (Bm-CPV) for a further 6 hours. Supernatants were then assessed for mature IL1β secretion by ELISA. All is representative of n=3 performed in triplicate.

Figure 3A:
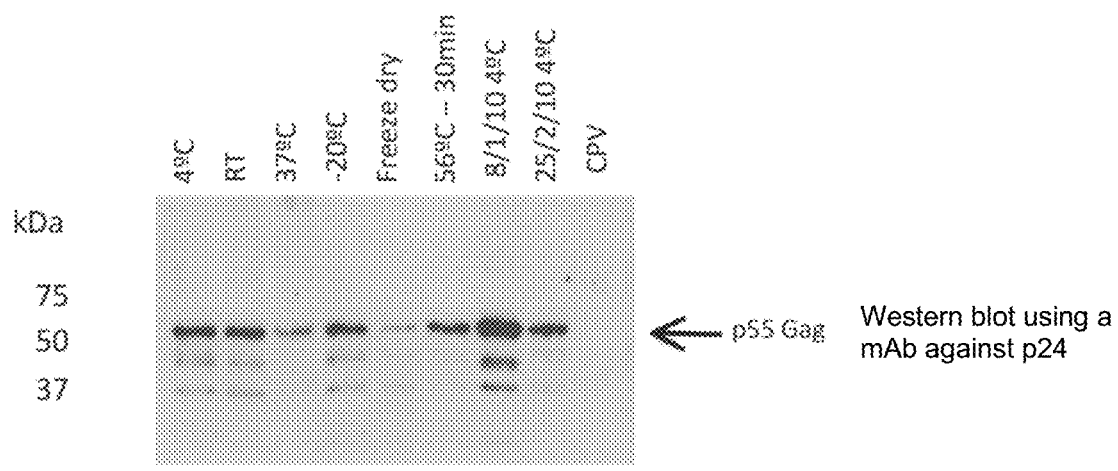
FIGS. 3A and 3B are photographic representations of data showing that Gag MicroCubes are highly stable under physiologically relevant conditions.

DETAILED DISCUSSION OF PARTICULAR EMBODIMENTS

The subject invention is not limited to particular screening procedures, specific formulations and various medical methodologies, as such may vary.

Unless defined otherwise, all technical and scientific terms used herein have the same meanings as commonly understood by one of ordinary skill in the art to which this invention belongs. Any materials and methods similar or equivalent to those described herein can be used to practise or test the present invention. Practitioners are particularly directed to Ream et al., eds., *Molecular Biology Techniques: An Intensive Laboratory Course,* Academic Press, 1998; Newton and Graham eds., *PCR, Introduction to Biotechniques Series, 2nd ed.,* Springer Verlag, 1997; Sambrook et al., *Molecular Cloning: A Laboratory Manual,* Cold Spring Harbor Laboratory, Cold Spring Harbor, N.Y., 1989, Coligan et al., *Current Protocols in Protein Science,* John Wiley & Sons, Inc. 1995-1997, in particular Chapters 1, 5 and 6, and Ausubel et al., *Cell Immunol.,* 193(1): 99-107, 1999; Colowick and Kaplan, eds., *Methods In Enzymology,* Academic Press, Inc.; Weir and Blackwell, eds., *Handbook of Experimental Immunology,* Vols. I-IV, Blackwell Scientific Publications, 1986; Joklik ed., *Virology, 3rd Edition,* 1988; Fields and Knipe, eds, *Fundamental Virology, 2nd Edition,* 1991; Fields et al., eds, *Virology, 3rd Edition,* Lippincott-Raven, Philadelphia, Pa., 1996; Mori et al., *J. Gen. Virol.* 74(1): 99-102, 1993; Ikeda et al., 2006 (supra); US Publication No. 2006/0155114; International Publication No. WO 2008/1105672.

Reference herein to a virus or viral antigen includes without limitation a virus or antigen therefrom from any virus family. Non-limiting examples of viral families include Adenoviridae, African swine fever-like viruses, Arenaviridae, Arterivirus, Astroviridae, Baculoviridae, Birnaviridae, Bunyaviridae, Caliciviridae, Circoviridae, Coronaviridae, Deltavirus, Filoviridae, Flaviviridae, Hepadnaviridae, Hepeviridae, Herpesviridae, Orthomyxoviridae, Paramyxoviridae, Picornaviridae, Poxyviridae, Reoviridae, Retroviridae and Rhabdoviridae. Particular viruses are from Paramyxoviridae, Retroviridae and Filoviridae.

In some embodiments, a virus includes a virus selected from influenza virus, respiratory syncytial virus (RSV), chlamydia, adenovirdiae, mastadenovirus, aviadenovirus, herpesviridae, herpes simplex virus 1, herpes simplex virus 2, herpes simplex virus 5, herpes simplex virus 6, leviviridae, levivirus, enterobacteria phase MS2, allolevirus, poxviridae, chordopoxvirinae, parapoxvirus, avipoxvirus, capripoxvirus, leporiipoxvirus, suipoxvirus, molluscipoxvirus, entomopoxvirinae, papovaviridae, polyomavirus, papillomavirus, paramyxoviridae, paramyxovirus, parainfluenza virus 1, mobillivirus, measles virus, rubulavirus, mumps virus, pneumonovirinae, pneumovirus, metapneumovirus, avian pneumovirus, human metapneumovirus, picornaviridae, enterovirus, rhinovirus, hepatovirus, human hepatitis A virus, cardiovirus, andapthovirus, reoviridae, orthoreovirus, orbivirus, rotavirus, cypovirus, fijivirus, phytoreovirus, oryzavirus, retroviridae, mammalian type B retroviruses, mammalian type C retroviruses, avian type C retroviruses, type D retrovirus group, BLV-HTLV retroviruses, lentivirus, human immunodeficiency virus 1, human immunodeficiency virus 2, spumavirus, flaviviridae, hepatitis C virus, hepadnaviridae, hepatitis B virus, togaviridae, alphavirus sindbis virus, rubivirus, rubella virus, rhabdoviridae, vesiculovirus, lyssavirus, ephemerovirus, cytorhabdovirus, necleorhabdovirus, arenaviridae, arenavirus, lymphocytic choriomeningitis virus, Ippy virus, lassa virus, coronaviridae, coronavirus and torovirus.

Illustrative viral pathogens include HIV, HSV, chlamydia, SARS, RSV, Dengue virus and Influenza. Another illustrative pathogen is an apicomplexal parasite such as *Plasmodium* Spp. The antigen or a pathogen or condition may be combined with a polyhedrin targeting polypeptide in accordance with various aspects of the present invention.

In particular embodiments, the antigen is a polypeptide or peptide proposed to engender or facilitate the production of an effective immune response in at least some subjects. Without being bound by any particular theory or mode of action, it is proposed that the present complexes stabilise and or protect the three dimensional structure of the antigen and provide improved vehicles for effective immune response production, for antibody and in some embodiments neutralising antibody production and for immune response and antibody screening. In preparing antibodies for diagnosis or screening, an effective immune response is generally one that producing antibodies of sufficient affinity to be useful reagents in standard protocols employing antibodies, such as ELISA, RIA, RAPID, etc. In some embodiments, the antigen is recognised in the art as useful or potentially useful for generating a protective or neutralising immune response. A range of illustrative known target antigens are described herein. In other embodiments, the invention permits the characterisation of new useful antigens and conformational epitopes recognised, for example, by neutralising antibodies from infected subjects.

Any viral or non-viral antigen of a pathogen or cancer may be engineered using the methods described or referenced in this specification.

An “antigen” or “immunogen” or “antigenic” or “immunogenic” refers to a molecule containing one or more epitopes (either linear, conformational or both) that will stimulate an immune system to make a humoral and/or cellular antigen-specific response. Generally, a B-cell epitope will include at least about 5 amino acids but can be as small as 3-4 amino acids. A T-cell epitope, such as a cytolytic T-cell (CTL) epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term “antigen” denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. The "antigen" may comprise one or more epitopes of one or more species, subspecies, types, clades, variants, isolates, etc. and/or one or more pathogens and/or one or more cancer antigens. In some embodiments, reference to "antigen" does not include human or mammalian antigens encoded by a nucleic acid molecule expressed in humans, other than tumor antigens. In some embodiments "antigen" does not include antigens encoded by indigenous nucleic acid molecules expressed in humans.

Illustrative antigens include those selected from influenza virus haemagglutinin, human respiratory syncytial virus G glycoprotein, core protein, matrix protein or other protein of Dengue virus, measles virus haemagglutinin, herpes simplex virus type 2 glycoprotein gB, poliovirus I VP1, envelope or capsid glycoproteins of HIV-I or HIV-II, hepatitis B surface antigen, diptheria toxin, streptococcus 24M epitope, gonococcal pilin, pseudorabies virus g50 (gpD), pseudorabies virus II (gpB), pseudorabies virusgIII (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, Serpulinahydodysenteriae protective antigen, bovine viral diarrhea glycoprotein 55, newcastle disease virus hemagglutinin-neuraminidase, swine flu hemagglutinin, swine flu neuraminidase, foot and mouth disease virus, hog colera virus, swine influenza virus, African swine fever virus, mycoplasma liyopneutiioniae, infectious bovine rhinotracheitis virus, infectious bovine rhinotracheitis virus glycoprotein E, glycoprotein G, infectious laryngotracheitis virus, infectious laryngotracheitis virus glycoprotein G or glycoprotein I, a glycoprotein of La Crosse virus, neonatal calf diarrhoea virus, Venezuelan equine encephalomyelitis virus, punta toro virus, murine leukemia virus, mouse mammary tumor virus, hepatitis B virus core protein and hepatitis B virus surface antigen or a fragment or derivative thereof, antigen of equine influenza virus or equine herpes virus, including equine influenza virus type A/Alaska 91 neuraminidase, equine influenza virus typeA/Miami 63 neuraminidase, equine influenza virus type A/Kentucky 81 neuraminidase equine herpes virus type 1 glycoprotein B, and equine herpes virus type 1 glycoprotein D, antigen of bovine respiratory syncytial virus or bovine parainfluenza virus, bovine respiratory syncytial virus attachment protein (BRSV G), bovine respiratory syncytial virus fusion protein (BRSV F), bovine respiratory syncytial virus nucleocapsid protein (BRSVN), bovine parainfluenza virus type 3 fusion protein, bovine parainfluenza virus type 3 hemagglutinin neuraminidase, bovine viral diarrhoea virus glycoprotein 48 and glycoprotein 53.

Illustrative cancer antigens include KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens, CEA, TAG-72, LEA, Burkitt's lymphoma antigen-38.13, CD19, human B-lymphoma antigen-CD20, CD33, melanoma specific antigens, ganglioside GD2, ganglioside GD3, ganglioside GM2, ganglioside GM3, tumor-specific transplantation type of cell-surface antigen (TSTA), virally-induced tumor antigens, T-antigen DNA tumor viruses, envelope antigens of RNA tumor viruses, oncofetal antigen-alpha-fetoprotein, CEA of colon, bladder tumor oncofetal antigen, differentiation antigen, human lung carcinoma antigen L6, L20, antigens of fibrosarcoma, human leukemia T cell antigen-Gp37, neoglycoprotein, sphingolipids, breast cancer antigen, EGFR (Epidermal growth factor receptor), HER2 antigen, polymorphic epithelial mucin, malignant human lymphocyte antigen-APO-1, differentiation antigen, including I antigen found in fetal erythrocytes, primary endoderm, I antigen found in adult erythrocytes, preimplantation embryos, I (Ma) found in gastric adenocarcinomas, M18, M39 found in breast epithelium, SSEA-1 found in myeloid cells, VEP8, VEP9, Myl, VIM-D5, Du56-22 found in colorectal cancer, TRA-1-85 (blood group H), C14 found in colonic adenocarcinoma, F3 found in lung adenocarcinoma, AH6 found in gastric cancer, Y hapten, LeY found in embryonal carcinoma cells, TL5 (blood group A), EGF receptor found in A431 cells, E1 series (blood group B) found in pancreatic cancer, FC10. 2 found in embryonal carcinoma cells, gastric adenocarcinoma antigen, CO-514 (blood group Lea) found in Adenocarcinoma, NS-10 found in adenocarcinomas, CO-43 (blood groupLeb), G49 found in EGF receptor of A431 cells, MH2 (blood groupALeb/Ley) found in colonic adenocarcinoma, 19.9 found in colon cancer, gastric cancer mucins, TsA7 found in myeloid cells, R24 found in melanoma, 4.2, GD3, D1.1, OFA-1, GM2, OFA-2, GD2, and M1:22:25:8 found in embryonal carcinoma cells, and SSEA-3 and SSEA-4 found in 4 to 8-cell stage embryos.

Non-viral pathogens and antigens further include those from pathogenic or non-pathogenic fungi, including parasites, including apicomplexa, or uni cellular parasites, nematodes, trematodes, cestodes and plant pathogen or parasitic bacteria.

In an illustrative embodiment, one important group of pathogens is the primary systemic fungal pathogens of man such *Coccidioides immitis, Histoplasma capsulatum, Blastomyces dermatitidis,* and *Paracoccidioides brasiliensis.* Important opportunistic fungal pathogens which tend to rely upon an immunocompromised host include *Cryptococcus neoformans, Pneumocystis jiroveci, Candida* spp., *Aspergillus* spp., *Penicillium marneffei,* and Zygomycetes, *Trichosporon beigelii,* and *Fusarium* spp. A range of pathogenic fungi are associated with immunocompromised subjects including those with AIDS, with chemotherapy induced neutropenia or patients undergoing haematopoietic stem cell transplantation, among others.

In some embodiments, the pathogen is a microbe including a bacterium, fungus, virus, algae, parasite, (including ecto-or endo-parasites) prion, oomycetes, slime, moulds, nematode, mycoplasma and the like. By way of non-limiting example, the microbe is selected from one or more of the following orders, genera or species: *Acinetobacter, Actinobacillus, Actinomycetes, Actinomyces, Aeromonas, Bacillus, Bacteroides, Bordetella, Borrelia, Brucella, Burkholderia, Campylobacter, Citrobacter, Clostridium, Corynebacterium, Enterobacter, Enterococcus, Erysipelothrix, Escherichia, Francisella, Haemophilus, Helicobacter, Klebsiella, Legionella, Leptospira, Listeria, Micrococcus, Moraxella, Morganella, Mycobacterium* (tuberculosis), *Nocardia, Neisseria, Pasteurella, Plesiomonas, Propionibacterium, Proteus, Providencia, Pseudomonas, Rhodococcus, Salmonella, Serratia, Shigella, Staphylococcus, Stenotrophomonas, Streptococcus, Treponema, Vibrio* (cholera) and *Yersinia* (plague), *Adenoviridae,* African swine fever-like viruses, *Arenaviridae* (such as viral *haemorrhagic* fevers, Lassa fever), *Astroviridae* (astroviruses) *Bunyaviridae* (La Crosse), *Calicivirid* (Norovirus), *Coronaviridae* (Corona virus), *Filoviridae* (such as Ebola virus, Marburg virus), *Parvoviridae* (B19 virus), *Flaviviridae* (such as hepatitis C virus, Dengue viruses), *Hepadnaviridae* (such as hepatitis B virus, *Deltavirus*), *Herpesviridae* (herpes simplex virus, varicella zoster virus), *Orthomyxoviridae* (influenza virus) *Papovaviridae* (papilloma virus) *Paramyxoviridae* (such as human *parainfluenza* viruses, mumps virus, measles virus, human respiratory syncytial virus) *Picornaviridae* (common cold virus), *Poxviridae* (small pox virus, *orf* virus, monkey poxvirus) *Reoviridae* (rotavirus) *Retroviridae* (human immunodeficiency virus) *Paroviridae* (paroviruses) *Papillomaviridae*, (papillomaviruses) alphaviruses and *Rhabdoviridae* (rabies virus), *Trypanosoma, Leishmania, Giardia, Trichomonas, Entamoeba, Naegleria, Acanthamoeba, Plasmodium, Toxoplasma, Cryptosporidium, Isospora, Balantidium, Schistosoma, Echinostoma, Fasciolopsis, Clonorchis, Fasciola, Opisthorchis* and *Paragonimus*, Pseudophyllidea (e.g., *Diphyllobothrium*) and Cyclophyllidea (e.g., *Taenia*). Pathogenic nematodes include species from the orders; Rhabditida (e.g., *Strongyloides*), Strongylida (e.g., *Ancylostoma*), Ascarida (e.g., *Ascaris, Toxocara*), Spirurida (e.g., *Dracunculus, Brugia, Onchocerca, Wucheria*), and Adenophorea (e.g., *Trichuris* and *Trichinella*), *Prototheca* and *Ptiesteria, Absidia, Aspergillus, Blastomyces, Candida* (yeast), *Cladophialophera, Coccidioides, Cryptococcus, Cunninghamella, Fusarium, Histoplasma, Madurella, Malassezia, Microsporum, Mucor, Paecilomyces, Paracoccidioides, Penicillium, Pneumocystis, Pseudallescheria, Rhizopus, Rhodotorula, Scedosporium, Sporothrix, Trichophyton* and *Trichosporon*. For the avoidance of doubt the pathogen may include an emerging or re-emerging pathogen or an organism which has never previously been identified as a pathogen in a particular subject.

Reference herein to "bound" includes covalent and non-covalent bonds. In illustrated embodiments, the bond is a covalent bond, such as between linear components of a fusion protein. Another covalent bond is a disulphide base. "Fused" refers to a covalent bond.

"Synthetic" sequences, as used herein, include polynucleotides whose expression has been optimized as described herein, for example, by codon substitution, deletions, replacements and/or inactivation of inhibitory sequences usually in order to optimize expression. "Wild-type" or "native" or "naturally occurring" sequences, as used herein, refers to polypeptide encoding sequences that are essentially as they are found in nature.

Recombinant polypeptides and antigens can be conveniently prepared using standard protocols as described for example in Sambrook, et al., 1989 (supra), in particular Sections 16 and 17; Ausubel et al., 1994 (supra), in particular Chapters 10 and 16; and Coligan et al., Current Protocols in Protein Science, John Wiley & Sons, Inc. 1995-1997, in particular Chapters 1, 5 and 6. Fusion proteins comprising polyhedrin targeting peptides and expressing vectors encoding polyhedrin such as AcCP-H are described in Ikeda et al., 2006 (supra); US Publication No. 2006/0155114; Mori et al., 1993 (supra); International Publication No. WO 2008/1105672. The polypeptides or polynucleotides may be synthesized by chemical synthesis, e.g., using solution synthesis or solid phase synthesis as described, for example, in Chapter 9 of Atherton and Shephard (supra) and in Roberge et al., Science, 269(5221): 202-204, 1995.

Pharmaceutical compositions are conveniently prepared according to conventional pharmaceutical compounding techniques. See, for example, Remington's Pharmaceutical Sciences, 18th Ed., Mack Publishing, Company, Easton, Pa., U.S.A., 1990. The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g. intravenous, oral or parenteral.

A "pharmaceutically acceptable carrier" and/or a diluent is a pharmaceutical vehicle comprised of a material that is not otherwise undesirable i.e., it is unlikely to cause a substantial adverse reaction by itself or with the active agent. Carriers may include all solvents, dispersion media, coatings, antibacterial and antifungal agents, agents for adjusting tonicity, increasing or decreasing absorption or clearance rates, buffers for maintaining pH, chelating agents, membrane or barrier crossing agents. A pharmaceutically acceptable salt is a salt that is not otherwise undesirable. The agent or composition comprising the agent may be administered in the form of pharmaceutically acceptable non-toxic salts, such as acid addition salts or metal complexes, For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. Tablet may contain a binder such as tragacanth, corn starch or gelatin; a disintegrating agent, such as alginic acid; and a lubricant, such as magnesium stearate. If desired, tablets may be sugar-coated or enteric-coated by standard techniques. The active agent can be encapsulated to make it stable to passage through the gastrointestinal tract. See for example, International Patent Publication No. WO 96/11698.

For parenteral administration, the composition may be dissolved in a carrier and administered as a solution or a suspension. When the agents are administered intrathecally, they may also be dissolved in cerebrospinal fluid. For transmucosal or transdermal (including patch) delivery, appropriate penetrants known in the art are used for delivering the subject complexes. For inhalation, delivery uses any convenient system such as dry powder aerosol, liquid delivery systems, air jet nebulizers, propellant systems. For example, the formulation can be administered in the form of an aerosol or mist. The agents may also be delivered in a sustained delivery or sustained release format. For example, biodegradable microspheres or capsules or other polymer configurations capable of sustained delivery can be included in the formulation. Formulations can be modified to alter pharmacokinetics and biodistribution. For a general discussion of pharmacokinetics, see, e.g., Remington's. In some embodiments the formulations may be incorporated in lipid monolayers or bilayers such as liposomes or micelles. Targeting therapies known in the art may be used to deliver the agents more specifically to certain types of cells or tissues such as, without limitation, antigen presenting cells.

The actual amount of active agent administered and the rate and time-course of administration will depend on the nature and severity of the disease or condition. Prescription of treatment, e.g. decisions on dosage, timing, etc. is within the responsibility of general practitioners or specialists and typically takes into account the condition of the individual patient, the site of delivery, the method of administration and other factors known to practitioners. Examples of techniques and protocols can be found in Remington's Pharmaceutical Sciences (supra).

Sustained-release preparations that may be prepared are particularly convenient for inducing immune responses. Examples of sustained-release preparations include semipermeable matrices of solid hydrophobic polymers containing the antagonist, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers, and poly-D-(–)-3-hydroxybutyric acid. While polymers such as ethylene-vinyl acetate and lactic acid-glycolic acid enable release of molecules for over 100 days, certain hydrogels release proteins for shorter time periods. Liposomes may be used which are of the small (about 200-800 Angstroms) unilamellar type in which the lipid content is greater than about 30% cholesterol, the selected proportion being adjusted for the optimal therapy.

Stabilization of proteins may be achieved by modifying sulfhydryl residues, lyophilizing from acidic solutions, controlling moisture content, using appropriate additives, and developing specific polymer matrix compositions. The in vivo half life of proteins may be extended using techniques known in the art, including, for example, by the attachment of other elements such as polyethyleneglycol (PEG) groups.

Prime-boost immunisation strategies as disclosed in the art are clearly contemplated. See for example International Publication No. WO/2003/047617. Thus, compositions may be in the form of a vaccine, priming or boosting agent.

Instead of administering the protein complex directly, they could be produced in a host cell or an introduced cell, e.g. in a viral vector or in a cell based delivery system. The vector could be targeted to elements of the immune system. A cell based delivery system is designed to be implanted in a patient's body at a desired target site and contains coding sequences for the subject fusion polypeptides, complexes and polyhedra. Alternatively, the agent could be administered in a precursor form for conversion to the active form by an activating agent produced in, or targeted to, the cells to be treated.

In further describing the various applications of the subject compositions in eliciting immune responses, the compositions is generally administered in an effective amount and for a time an under conditions sufficient to elicit an immune response. The compositions of the present invention may be administered as a single dose. Alternatively, the compositions may involve repeat doses or applications.

The terms "effective amount" including a "therapeutically effective amount" and "prophylactically effective amount" as used herein mean a sufficient amount a composition comprising a complex as defined herein, or a cell or antibody as described herein, which provides the desired therapeutic or physiological effect and is an amount sufficient to achieve a biological effect such as to induce enough humoral or cellular immunity. Desired biological effects include but are not limited to reduced or no symptoms, remission, reduced pathogen titres, reduced vascular or cerebral compromise, reduced nasal secretions, fever etc. Undesirable effects, e.g. side effects, may sometimes manifest along with the desired therapeutic effect; hence, a practitioner balances the potential benefits against the potential risks in determining an appropriate "effective amount". The exact amount of agent required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine experimentation. One of ordinary skill in the art would be able to determine the required amounts based on such factors as prior administration of agents, the subject's size, the severity of the subject's symptoms, pathogen load, and the particular composition or route of administration selected.

The terms "treatment" or "prophylaxis" or "therapy" are used interchangeably in their broadest context and include any measurable or statistically significant amelioration in at least some subjects in one or more symptoms of a condition to be treated or in the risk of developing a particular condition. Prophylaxis may be considered as reducing the severity or onset of a condition or signs of a condition. Treatment may also reduce the severity of existing conditions. The administration of a vaccine composition is generally for prophylactic purposes.

In some embodiments, a vaccine or composition of the present invention is physiologically effective if its presence results in a detectable change in the physiology of a recipient patient that enhances or indicates an enhancement in at least one primary or secondary humoral or cellular immune response against at least one strain of an pathogen or virus. In some embodiments the vaccine composition is administered to protect against infection by a pathogen. The "protection" need not be absolute, i.e., the infection need not be totally prevented or eradicated, if there is a statistically significant improvement compared with a control population or set of patients. Protection may be limited to reducing the severity or rapidity of onset of symptoms of the viral or other pathogen infection, or the development of cancer or other condition as described herein.

In one embodiment, a vaccine composition of the present invention is provided to a subject either before the onset of infection (so as to prevent or attenuate an anticipated infection) or after the initiation of an infection, and thereby protects against viral infection. In some embodiments, a vaccine composition of the present invention is provided to a subject before or after onset of infection, to reduce viral transmission between subjects.

It will be further appreciated that compositions of the present invention can be administered as the sole active pharmaceutical agent, or used in combination with one or more agents to treat or prevent pathogen infections or symptoms associated with such infection.

The pharmaceutical composition is contemplated to exhibit therapeutic activity when administered in an amount that depends upon the particular case. The variation depends, for example, on the human or animal and the agent chosen. A broad range of doses may be applicable. Considering a subject, for example, from about 0.1 µg to 1 µg (i.e., including 0.1 µg, 0.2 µg, 0.3 µg, 0.4 µg, 0.5 µg, 0.6 µg, 0.7 µg, 0.8 µg and 0.9 µg) 0.5 µg to 50 µg, 1 µg to 10 µg, 2 µg to 200 µg, 0.1 mg to 1.0 mg (i.e., including 0.1 mg, 0.2 mg, 0.3 mg, 0.4 mg, 0.5 mg, 0.6 mg, 0.7 mg, 0.8 mg and 0.9 mg), from about 15 mg to 35 mg, about 1 mg to 30 mg or from 5 to 50 mg, or from 10 mg to 100 mg of agent may be administered per kilogram of body weight per day or per every other day or per week or per month. Therapeutic including prophylactic compositions may be administered at a dosage of about 0.1 to 20 mg/kg however dosages above or below this amount are contemplated in the ranges set out above. Dosage regimes may be adjusted to provide the optimum therapeutic response. For example, several divided doses may be administered daily, weekly, monthly or other suitable time intervals or the dose may be proportionally reduced as indicated by the exigencies of the situation. It is also possible to administer compositions in sustained release formulations. Pharmaceutical preparations are conveniently provided in unit dosage form such as tablets, capsules, powders etc.

The compositions, complexes, antibodies and cells may be administered in a convenient manner such as by the oral, intravenous, intraperitoneal, intramuscular, subcutaneous, intradermal, intrathecal or suppository routes or implanting (e.g. using slow release molecules). Administration may be systemic or local. References to systemic include intravenous, intraperitoneal, subcutaneous injection, infusion as well as administration via oral, rectal, vaginal and nasal routes or via inhalation. Other contemplated routes of administration are by patch, cellular transfer, implant, sublingually, intraocularly, topically or transdermally.

In some embodiments, oral or nasal administration is contemplated. Capillaries have a diameter or approximately 5 μm permitting administration of complexes that are smaller than about 1 μm diameter. Polyhedra of more than 5 μm may be administered subcutaneously or intra muscularly or by other convenient route known in the art. Polyhedra can routinely be separated based upon size.

Functional variants and derivatives include "biologically active portion" or "biologically active part" or "functional part or portion" by which is meant a portion of a full-length targeting polypeptides which portion retains the activity of the full length molecule at least in so far as it retains the structural and functional abilities to target an antigen to polyhedrin. As used herein, the term "biologically active portion" includes deletion mutants and peptides, for example of at least about 20 to 200 amino acids, such as 20, 21, 22, 23, 24, 25, 30, 40, 50, 60, 70, 80, 90, 100, 120, 150, 300, 350 contiguous amino acids (and every integer in between), which retains activity. Portions of this type may be obtained through the application of standard recombinant nucleic acid techniques or synthesized using conventional or state of the art liquid or solid phase synthesis techniques. For example, reference may be made to solution synthesis or solid phase synthesis as described, for example, in Chapter 9 entitled By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a targeting polypeptide including additions, or deletions that provide for functionally equivalent molecules.

A "part" or "portion" of a polynucleotide or polypeptide is defined as having a minimal size of at least about 20 nucleotides or amino acids and may have a minimal size of at least about 100 nucleotides or amino acids. This definition includes all sizes in the range of 10-35 nucleotides or amino acids including 10, 11, 12, 13, 14, 15, 16, 17, 18, 19, 20, 21, 22, 23, 24, 25, 26, 27, 28, 29, 30, 31, 32, 33, 34 or 35 nucleotides or amino acids as well as greater than 100 nucleotides or amino acids including 300, 500, 600 nucleotides or amino acids or molecules having any number of nucleotides or amino acids within these values.

Reference herein to "functional variants" of targeting polypeptides or peptides or polyhedrin polypeptides include naturally or non-naturally occurring functional variants, biologically active parts or portions, precursors, derivatives, analogs and recombinant or synthetic forms having a degree of sequence similarity or the omission of one or more biologically active parts or portions sufficient to retain the functional and structural ability of the sequences identified herein to form complexes with polyhedrin as described herein. Functional variants are described further in the detailed description.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, Calif., USA) using standard defaults as used in the reference manual accompanying the software.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., *Nucl. Acids Res.,* 25: 3389-3402, 1997. A detailed discussion of sequence analysis can be found in Unit 19.3 of Ausubel et al., *Current Protocols in Molecular Biology,* John Wiley & Sons Inc, Chapter 15, 1994-1998.

The term "recombinant" may be used herein to describe a nucleic acid molecule and means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

"Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected.

"Hybridization" or "hybridize" is used herein to denote the pairing of complementary nucleotide sequences to produce a DNA-DNA hybrid or a DNA-RNA hybrid. Hybridization can occur under varying circumstances as known to those of skill in the art. The phrase "hybridizing specifically to" and the like refer to the binding, duplexing, or hybridizing of a molecule only to a particular nucleotide sequence under stringent conditions as known in the art.

The terms "antibody" and "antibodies" include polyclonal and monoclonal antibodies and all the various forms derived from monoclonal antibodies, including but not limited to full-length antibodies (e.g. having an intact Fc region), antigen-binding fragments, including for example, Fv, Fab, Fab' and F(ab')$_2$ fragments; and antibody-derived polypeptides produced using recombinant methods such as single chain antibodies. The terms "antibody" and "antibodies" as used herein also refer to human antibodies produced for example in transgenic animals or through phage display, as well as subject antibodies, santibodies, primatised antibodies or deimmunised antibodies. It also includes other forms of antibodies that may be therapeutically acceptable and antigen-binding fragments thereof, for example single domain antibodies derived from cartilage marine animals or Camelidae, or from libraries based on such antibodies. The selection of fragment or modified forms of the antibodies may also involve any effect the fragments or modified forms have on their half-lives.

The term "monoclonal antibody" is used herein to refer to an antibody obtained from a population of substantially homogeneous antibodies. That is, the individual antibodies comprising the population are identical except for naturally occurring mutations that may be present in minor amounts. The term "monoclonal" as used herein indicates the character of the antibody as being obtained from a substantially homogeneous population of antibodies, and is not used to indicate that the antibody was produced by a particular method. For example, monoclonal antibodies in accordance with the present invention may be made by the hybridoma method described by Kohler and Milstein, *Nature* 256:495-499, 1975, or may be made by recombinant DNA methods (such as described in U.S. Pat. No: 4,816,567). Monoclonal antibodies may also be isolated from phage antibody libraries using the techniques described in Clackson et al., *Nature* 352:624-628, 1991 or Marks et al., *J. Mol. Biol.* 222:581-597, 1991.

Vectors available for cloning and expression in host cell lines are well known in the art, and include but are not limited to vectors for cloning and expression in mammalian cell lines, vectors for cloning and expression in bacterial cell lines, vectors for cloning and expression in phage and vectors for cloning and expression insect cell lines. The antibodies can be recovered using standard protein purification methods.

Chemical analogs of antigens or polyhedrin molecules may be routinely employed where appropriate. Analogs contemplated herein include, but are not limited to, modifications of side chains, incorporation of unnatural amino acids and/or their derivatives during peptide, polypeptide or protein synthesis and the use of crosslinkers and other methods which impose conformational constraints on the proteinaceous molecule or their analogs.

The invention provides a method for producing an antibody comprising immunising a non-human animal or screening expression products of a library of human immunoglobulin genes with a fusion or complex protein or polyhedra as described herein, or a nucleic acid encoding same and isolating an antibody that binds specifically to the subject antigen or to all or part of a pathogen or tissue comprising same.

In another embodiment, the invention provides an antibody produced by the methods described herein using a subject protein or complex or a subject, human or humanised form thereof. The antibody is preferable monoclonal rather than polyclonal and is preferably subject, humanised, deimmunised or is a human antibody.

Reference to functional variants include those that are distinguished from a naturally-occurring form or from forms presented herein by the addition, deletion and/or substitution of at least one amino acid residue. Thus, variants include proteins derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is, they continue to possess the desired biological activity of the parent protein (e.g., immunogenicity or ability to form complexes with polyhedrin or encapsulate at least partially the antigen of interest). Variants may result from, for example, genetic polymorphism or from human manipulation. Biologically active variants of a viral polypeptide will typically have at least 40%, 50%, 60%, 70%, generally at least 75%, 80%, 85%, preferably about 90% to 95% or more, and more preferably about 98% or more sequence similarity or identity with the published amino acid sequence for the protein described herein as determined by sequence alignment programs described elsewhere herein using default parameters. In some embodiments, percentage identified refers to the full length polypeptide or to the parent molecule from which the variant is derived. A biologically active variant of a subject polypeptide may differ from that polypeptide generally by as much 100, 50 or 20 amino acid residues or suitably by as few as 1-15 amino acid residues, as few as 1-10, such as 6-10, as few as 5, as few as 4, 3, 2, or even 1 amino acid residue.

A variant polypeptide may be altered in various ways including amino acid substitutions, deletions, truncations, and insertions. Methods for such manipulations are generally known in the art. For example, amino acid sequence variants of a subject polypeptide can be prepared by mutations in the DNA. Methods for mutagenesis and nucleotide sequence alterations are well known in the art. See, for example, Kunkel, *Proc. Natl. Acad. Sci. USA,* 82: 488-492, 1985; Kunkel et al., *Methods in Enzymol.,* 154: 367-382, 1987; U.S. Pat. No. 4,873,192; Watson et al., *Molecular Biology of the Gene, Fourth Edition,* Benjamin/Cummings, Menlo Park, Calif., 1987) and the references cited therein. Guidance as to appropriate amino acid substitutions that do not affect biological activity of the protein of interest may be found in the model of Dayhoff et al., *Atlas of Protein Sequence and Structure,* Natl. Biomed. Res. Found., Washington, D.C., 1978. Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of subject polypeptides. Recursive ensemble mutagenesis (REM), a technique which enhances the frequency of functional mutants in the libraries, can be used in combination with the screening assays to identify subject polypeptide variants (Arkin and Yourvan, *Proc. Natl. Acad. Sci. USA,* 89: 7811-7815, 1992; Delgrave et al., *Protein Engineering,* 6: 327-331, 1993). Conservative substitutions, such as exchanging one amino acid with another having similar properties, are desirable as discussed in more detail below.

Variant subject polypeptides may contain conservative amino acid substitutions at various locations along their sequence, as compared to the reference amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al. 1978, (supra), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., *Science,* 256(5062): 1443-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic. Dependent on their structural properties, amino acid residues may fall in two or more classes. For the naturally-occurring protein amino acids, sub-classification according to this scheme is presented in the Table 1.

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional subject polypeptide can readily be determined by assaying its activity. Conservative substitutions are shown in Table 2 (below) under the heading of exemplary substitutions. More preferred substitutions are shown under the heading of preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Thus, a predicted non-essential amino acid residue in a subject polypeptide is typically replaced with another amino acid residue from the same side chain family. Alternatively, mutations can be introduced randomly along all or part of a subject polynucleotide coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined.

Accordingly, the present invention also contemplates variants of the subject polypeptides provided herein or their biologically-active fragments, wherein the variants are distinguished from the provided sequences by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity to a reference subject polypeptide sequence. Desirably, variants will have at least 30, 40, 50, 55, 60, 65, 70, 75, 80, 85, 90, 91, 92, 93, 94, 95, 96, 97, 98, 99% sequence identity to a parent subject polypeptide sequence. Moreover, sequences differing from the disclosed sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the biological activity of the parent subject polypeptide are contemplated. Variant subject polypeptides also include polypeptides that are encoded by polynucleotides that hybridize under stringency conditions as defined herein, especially high stringency conditions, to disclosed polynucleotide sequences, or the non-coding strand thereof.

In some embodiments, variant polypeptides differ from a prior art or wild-type sequence by at least one but by less than 50, 40, 30, 20, 15, 10, 8, 6, 5, 4, 3 or 2 amino acid residue(s). In another, variant polypeptides differ from the recited sequence by at least 1% but less than 20%, 15%, 10% or 5% of the residues. (If this comparison requires alignment the sequences should be aligned for maximum similarity. "Looped" out sequences from deletions or insertions, or mismatches, are considered differences.) The differences are, suitably, differences or changes at a non-essential residue or a conservative substitution.

A "non-essential" amino acid residue is a residue that can be altered from the wild-type sequence of an embodiment polypeptide without abolishing or substantially altering one or more of its activities. Suitably, the alteration does not substantially alter one of these activities, for example, the activity is at least 20%, 40%, 60%, 70% or 80% of wild-type. An "essential" amino acid residue is a residue that, when altered, results in abolition of an activity of the parent molecule such that less than 20% of the parent activity is present.

The present invention is further described by the following non-limiting Examples.

EXAMPLE 1

Material and Methods

Production of Gag Polyhedra
1) Split SF9 cells to a concentration of $1 \times 10^6$ cells/ml in 150-300ml SF-900 SFM (Invitrogen).
2) Add P3 viral stock CPV 1:500 and Gag Clone 15 P3 (H1-WT-Gag-His) 1:125 to the SF9 cells
3) Leave cells to incubate in the shaker at 27° C. for 48 h.
Purification of Polyhedra
1) Place the SF9 cell suspension in 50 ml Falcon tubes
2) Centrifuge at 2000 rpm for 5 min
3) Remove the supernatant
4) Add 1 ml sterile PBS (pH 7.4) to resuspend cells and transfer to an eppendorf tube
5) Sonicate the suspension for 30 sec at 10 mAmp on ice
6) Centrifuge at 4000 rpm for 1 min
7) Remove the supernatant and resuspend in 1 ml PBS
8) Repeat steps 5-7 another two times
9) Resuspend crystals in a final volume of 300 μl PBS
10) Check purity of polyhedra using a light microscope.
Purification using a Sucrose Gradient
1) Make up the following concentrations of sucrose in sterile $mQH_2 0$ as follows:

|  | Sucrose | $mQH_2 0$ |
| --- | --- | --- |
| 0.45% (w/w) | 9 g | 11 ml |
| 0.50% | 10 g | 10 ml |
| 0.55% | 11 g | 9 ml |
| 0.60% | 12 g | 8 ml |
| 0.65% | 13 g | 7 ml |

2) Using Beckman ultra clear 14×89 mm centrifuge tubes carefully layer 2 ml of 65% sucrose, followed by 2 ml 60% sucrose, 2 ml 55% sucrose, 2 ml 50% sucrose and 2 ml 45% sucrose
3) Make the total volume of polyhedra up to 1.5 ml in $mQH_2 0$ and add this to the top of the gradient
4) Using the TH-641 rotor, place balanced tubes in the ultracentrifuge and spin at 24000 rpm for 3 h at 4° C.
5) Remove tubes, and then carefully remove upper layers of sucrose with a 1 ml pipette
6) Remove the polyhedra layer (in 60% sucrose) in approximately 1.5 ml and place into an eppendorf tube.
Removal of Polyhedra from Sucrose
1) Using Slide-A-Lyzer Dialysis Cassettes (Thermo Scientific) hydrate the cassette in PBS for 1 min
2) Carefully insert 3 ml of the polyhedra/sucrose into the cassette using an 18 G needle as per the manufacturer's instructions
3) Remove all air from the membrane by pulling back on the syringe
4) Dialyse overnight in 500 ml sterile PBS
5) Fill the membrane with a small amount of air in a 18 G needle, and then collect the sample back out of the cassette
6) Place the sample which will have increased in volume into around 10 eppendorf tubes
7) Spin the eppendorf tubes at 10 000 rpm for 5 min 8) Remove PBS and resuspend the pellets in residual PBS. Total volume will be around 400 µl from two sucrose gradients.

Gag Western Blot
- SDS-Page gel is performed as per usual on a 15% Gel
- Protein is then transferred to a nitrocellulose membrane using transfer buffer—3.03 g tris base, 14.4 g glycine and 20% ethanol
- Membranes are blocked in 5% skim milk powder (blotto) in TBS-Tween overnight
- mAb 183 specific for p24 Gag is diluted 1:1000 in 5% blotto-TBS-T for 1 hour at RT
- Membrane is washed 3×5 min in TBS-T
- Anti-mouse Ig-HRP conjugated antibody (Chemicon) is added 1:10,000 diluted in 5% blotto- TBS-T for 1 hour at RT
- Membrane is washed 3×5 min in TBS-T
- Chemiluminescent detection using ECL-Plus reagent (GE Healthcare) and exposed to X-ray film.

Murine ELISPOT Protocol
Reagents:

| Description | Manufacturer | Cat Number |
| --- | --- | --- |
| ELISPOT antibody pairs | | |
| IFN-gamma (murine) | Mabtech | |
| AN18 (rat IgG1, coating) | | 3321-3-1000 (1 mg) |
| R4-6A2 (rat IgG1, detector) | | 3321-6-250 (250 µg) |
| IL-2 (murine) | Mabtech | |
| 1A12 (rat IgG2a) | | 3441-3-1000 (1 mg) |
| 5H4 (rat IgG2b) | | 3441-6-250 (250 µg) |
| IL-5 (murine) | Mabtech | |
| TRFK5 (rat IgG1) | | 3391-3-1000 (1 mg) |
| TRFK4 (rat IgG2a) | | 3391-6-250 (250 µg) |
| IFN-gamma (rat) | Mabtech | |
| rIFNg-I (mouse IgG1) | | 3220-3-1000 (1 mg) |
| rIFNg-II (mouse IgG1) | | 3220-6-250 (250 µg) |
| Streptavidin-alkaline phosphatase (1 mg) | Sigma | S2890 |
| BCIP/NBT liquid substrate (100 ml) | Sigma | B1911 |
| ELISPOT plates | Millipore | MSIPS4510 |
| PBS (without Mg and Calcium) | Invitrogen | 14190-250 |
| RPMI 1640, no glutamine (10 × 500 ml) | Invitrogen | 21870-092 |
| FCS | Invitrogen | 16000-044 |

Procedure—Example using IFN-γ antibody pairs, the same antibody concentrations are used for all antibody pairs.
ELISpot assay for the detection of IFN-γ
Preparation of plates.
1. Coat each 96 well (Millipore, multiscreen-IP 0.45 µm PVDF ELISPOT plates) with 100 µl per well of sterile PBS containing 5 µg/mL of anti-mouse IFN-γ mAb AN18.
2. Incubate overnight at 4° C.
3. Flick plate to remove mAb solution.
4. Wash plate 5 times with sterile PBS.
5. Blot plates on sterile paper towel (autoclavable).
6. Block plates with 200 µl per well of sterile RPMI+10% FCS.
7. Incubate at room temperature for one hour (can be longer if required).

Addition of splenocytes, peptide antigens and peptide pools.
8. Flick plates to remove blocking buffer and wash plates once with sterile PBS, may require two washes if block remains or bubbles.
9. Blot plates on sterile paper towel (autoclavable).
10. Use previously made up antigens (2 µg/mL, with the exception of CONA 8 µg/mL, final in the well concentration will be 1 µg/mL) in RPMI+10% FCS.
11. Place 50 µl per well of antigen and 50 µl per well of splenocyte cell suspension.
12. Incubate at 37° C. for 18-20 hours.

Plate Development.
13. Flick the plate to remove cells.
14. Wash 5 times with sterile PBS.
15. Add 100 µl per well of biotinylated mAb (1 µg/mL, RA-6A2), diluted in sterile PBS. Incubate at room temperature for 2 hours.
16. Wash 5 times with PBS.
17. Add 100 µl per well of streptavidin-alkaline phosphatase diluted to 1 µg/mL in sterile PBS. Incubate at room temperature for 1 hour.
18. Wash 5 times with sterile PBS.
19. Add 100 µl per well of BCIP/NBT liquid substrate (syringe filter just prior to use). Incubate at room temperature for 20-30 minutes, decided by the development of spots.
20. Flick plates and wash once with sterile DDH$_2$0 to end colour development and wash plates under a running tap.
21. Blot plates on paper towels and leave to dry overnight.

Important.
It is best to blot plates on paper towels (autoclavable) following each wash step, and before the addition of cells to reduce any possibility of diluting reagents.
All steps are done in a sterile hood
All washes are down with a multi-channel

EXAMPLE 2

Baculovirus HIV-1 Gag with an N-terminal H1 Sequence

A recombinant baculovirus transfer vector was constructed to encode various forms of HIV-1 Gag in frame with a nucleotide sequence of H1-helix of Bm-CPV polyhedrin (Ijiri et al., 2009 (supra)).

EXAMPLE 3

Production of Polyhedra Comprising HIV-1 Gag Antigen

A recombinant form of Bm-CPV (AcCP-H) which produces polyhedrin and further produces cubic polyhedra was used in this study (Mori et al., 1993 (supra)).
The H1 protein functions as a polyhedrin-recognition signal and Gag-H1 protein is incorporated together with polyhedrin into polyhedra Gag MicroCubes.

EXAMPLE 4

Immobilisation Of Gag Into Polyhedra

Polyhedra (Gag MicroCubes) were recovered and purified from the *Spodoptera frugiperda* cell line co-infected with AcCP-H which produces an HIV-1 polyhedrin, and a recombinant baculovirus expressing a Gag antigen as a fusion protein with H1-helix polypeptide sequence (optionally together with a detectable marker such as EGFP), sonication, successive washing steps and sucrose gradient purification.

Western blot analysis showed that Gag was successfully incorporated into polyhedra. Three bands could be detected which corresponded to full-length Gag (p55), Gag lacking p6, and p39. A mutant form of Gag, where dimer formation is inhibited, was incorporated into the polyhedra crystals at a similar level compared to wild-type Gag. Using both an ELISA and Western blotting an estimated amount of 10.9 µg of Gag protein was incorporated per mg of polyhedrin protein (FIGS. 1A-1D).

EXAMPLE 5

Stable Microcubes Are Produced

Figure 3B:
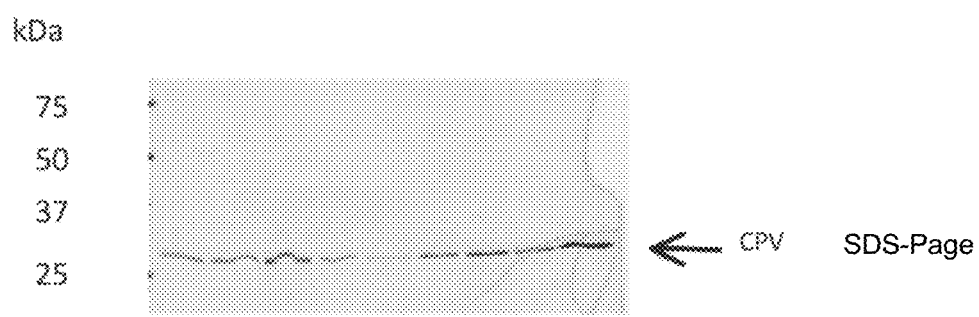
Figure 4A:
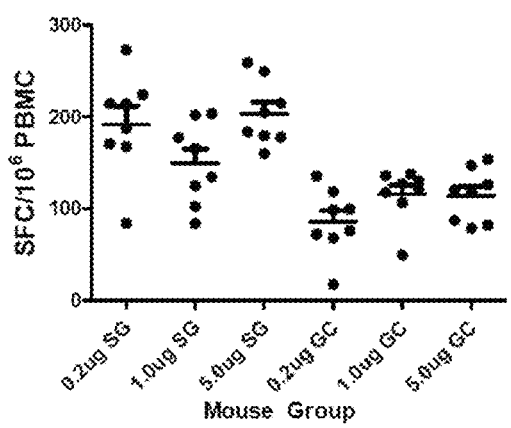
FIGS. 4A-4C are graphical representations of data showing IL-2 responses to full length HIV Gag, p39 and p24 peptides of HIV Gag.
Figure 4B:
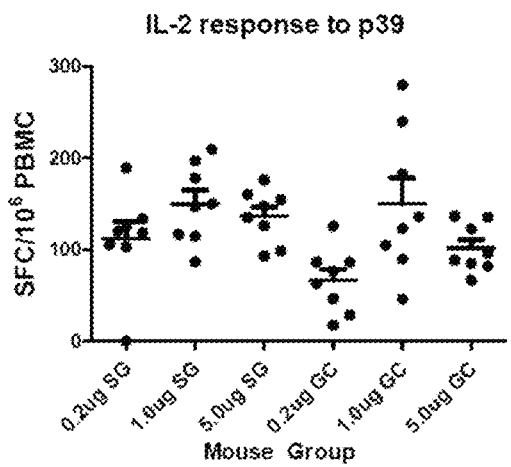
Figure 4C:
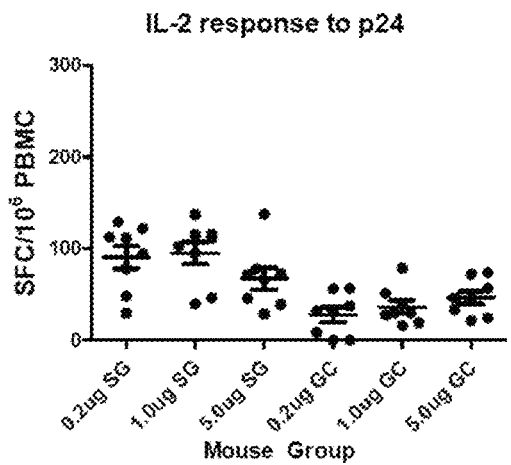
Figure 5A:
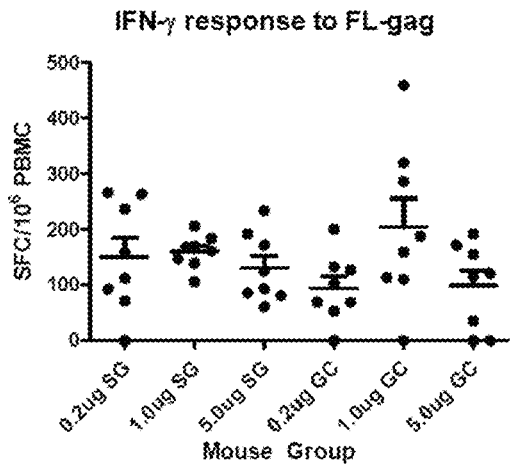
Figure 5B:
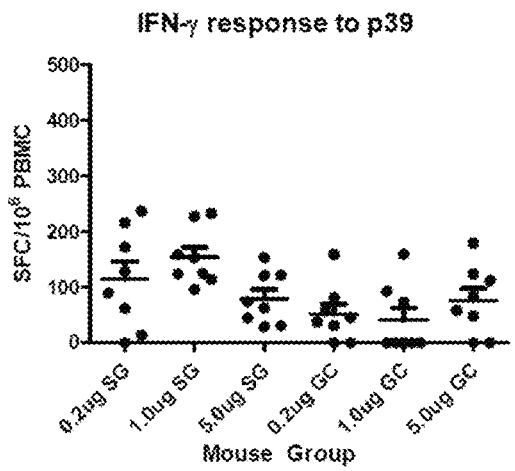
Figure 5C:
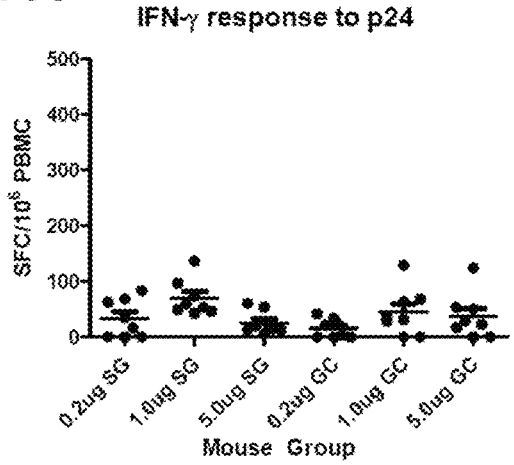
Figure 5D:
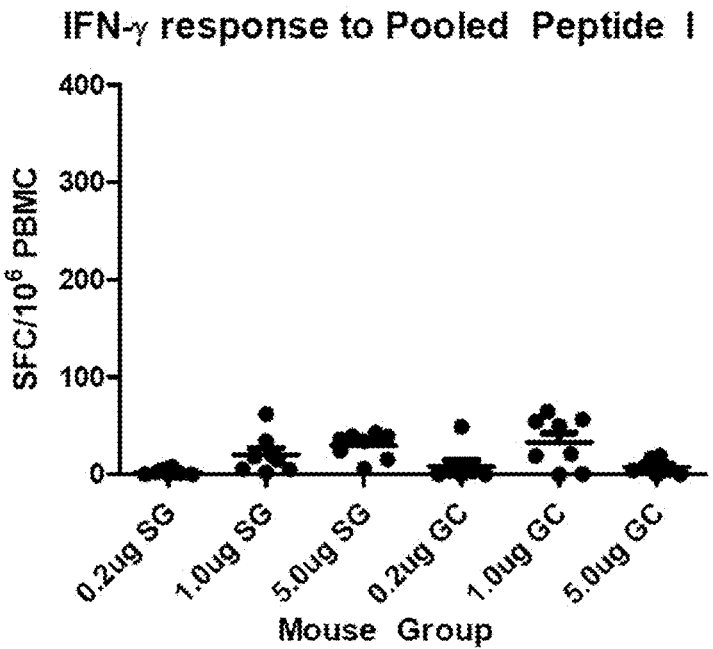
Figure 5E:
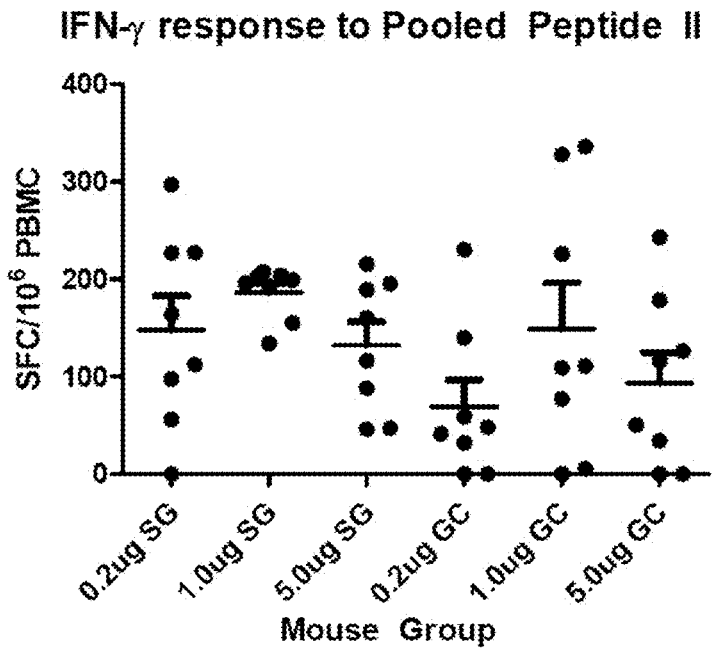
Figure 6A:
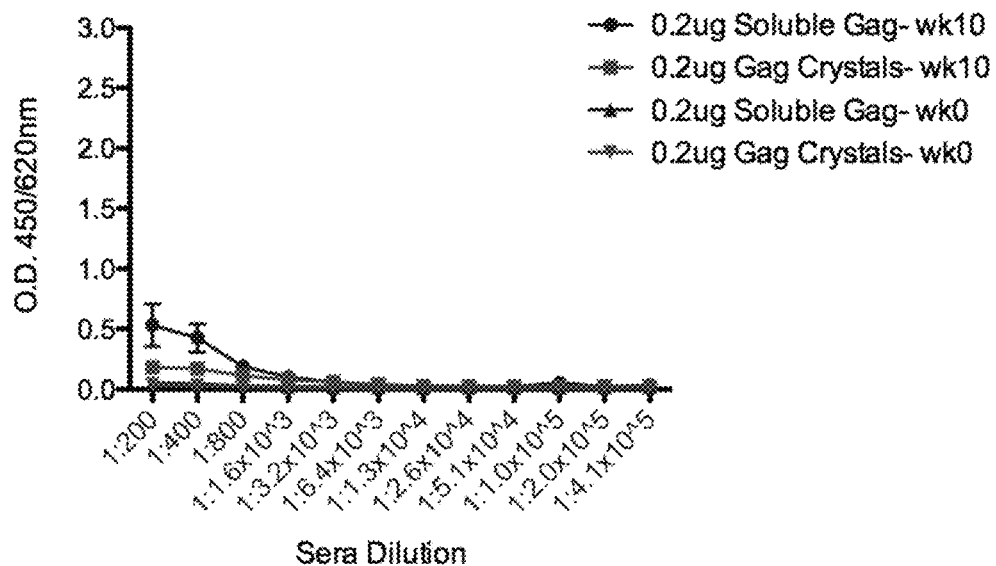
FIGS. 6A-6C are graphical representations of data showing antibody responses.
Figure 6B:
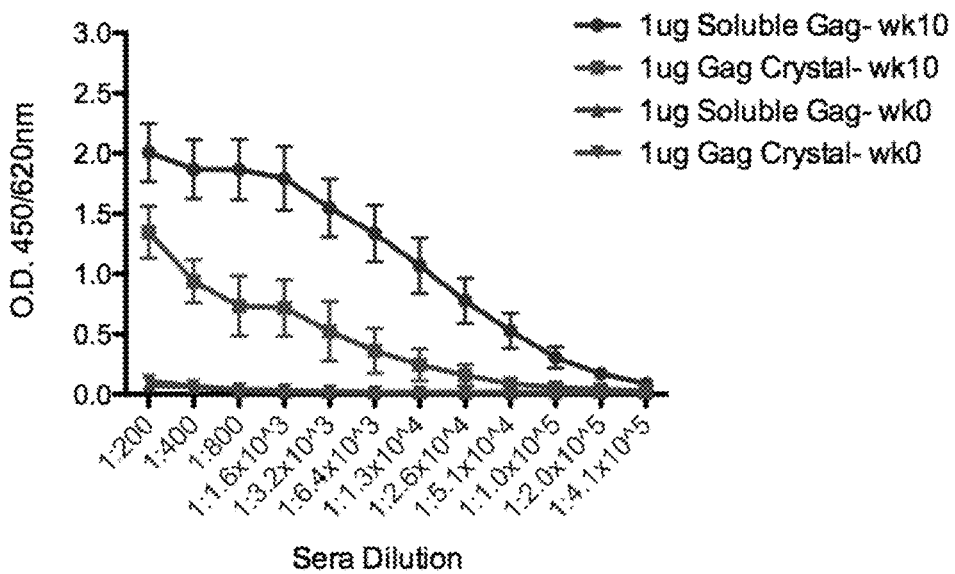
Figure 6C:
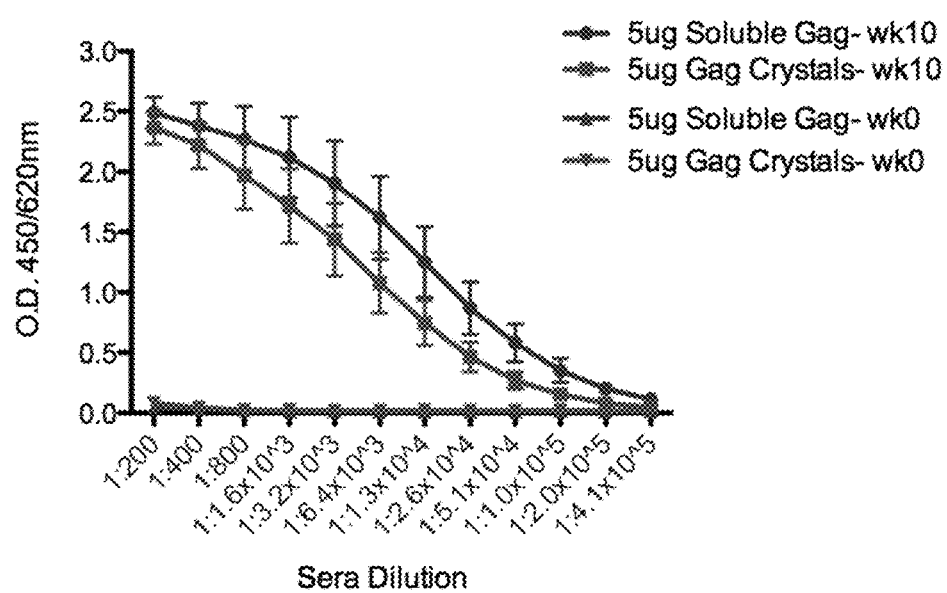
Figure 7A:
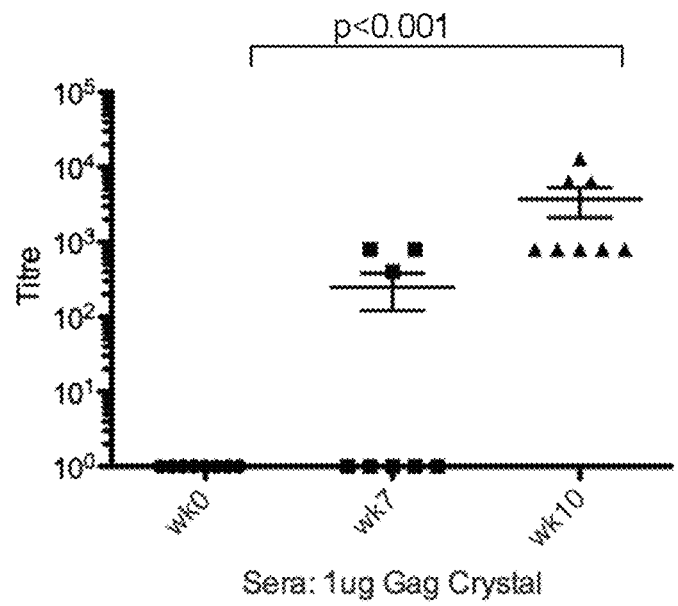
FIGS. 7A-7D are graphical representations of data showing end point titration.
Figure 7B:
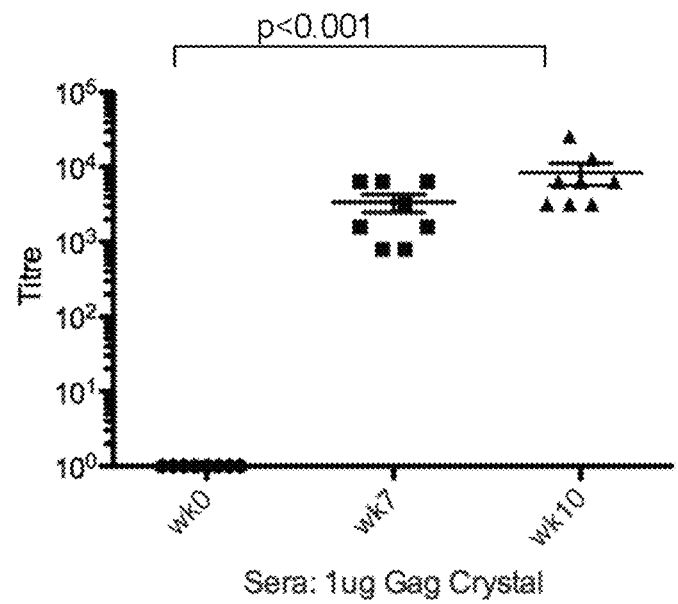
Figure 7C:
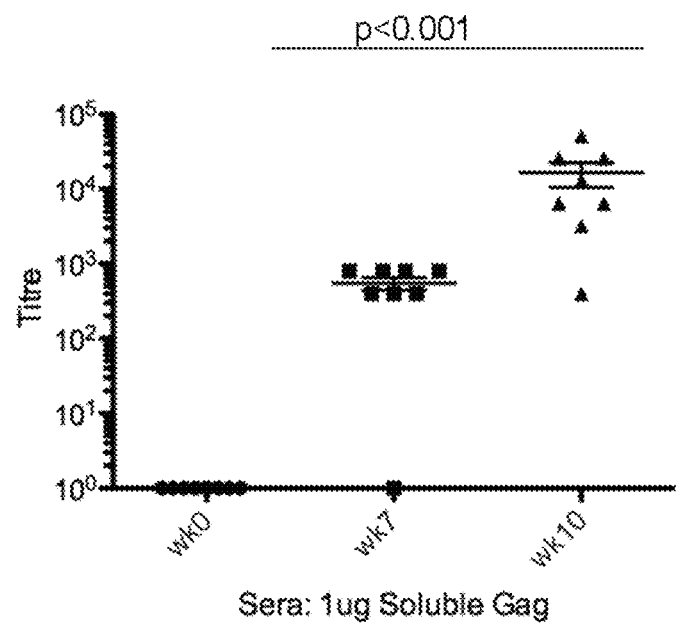
Figure 7D:
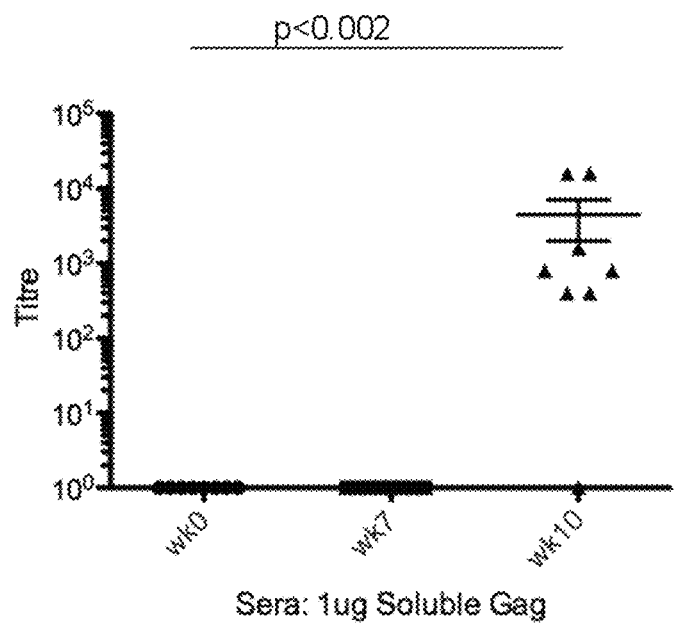
Figure 8:
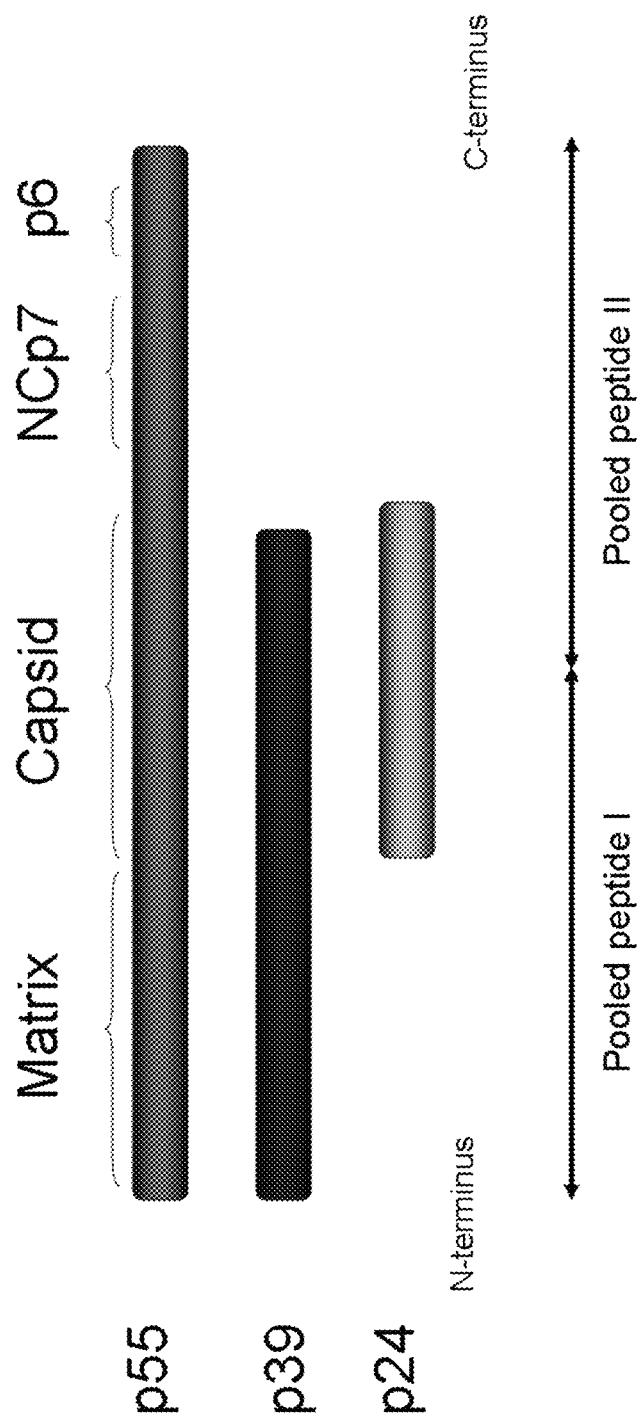
FIG. 8 is a schematic representation of peptides HIV-Gag.
Figures 10A, 10B:
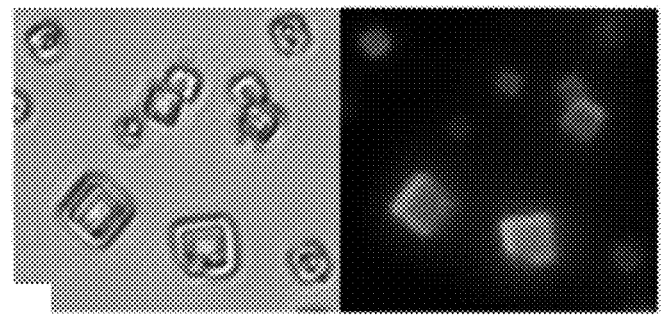
FIGS. 10A-10C are representations showing simultaneous incorporations of two antigens in MicroCubes.
Figure 10C:
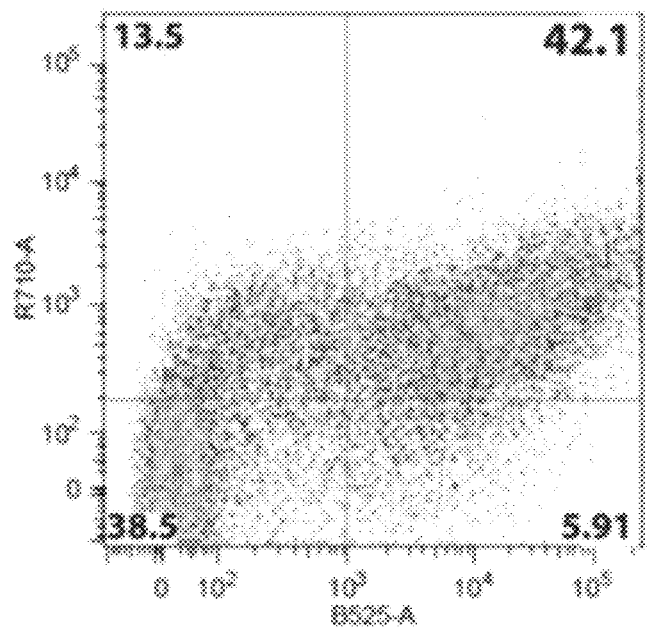
Figure 11A:
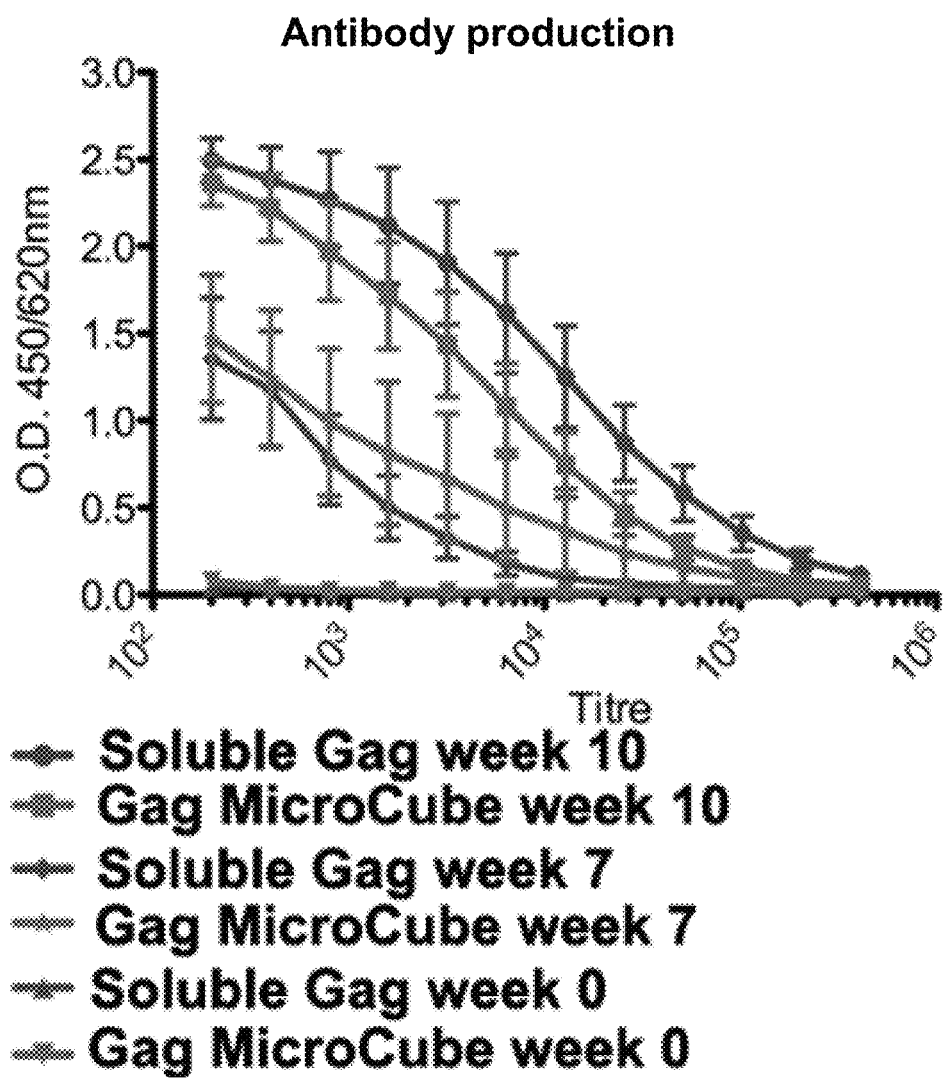
FIGS. 11A and 11B are graphical representations of robust humoral and cellular response to Gag MicroCubes in a mice immunogenicity experiment.
Figure 11B:
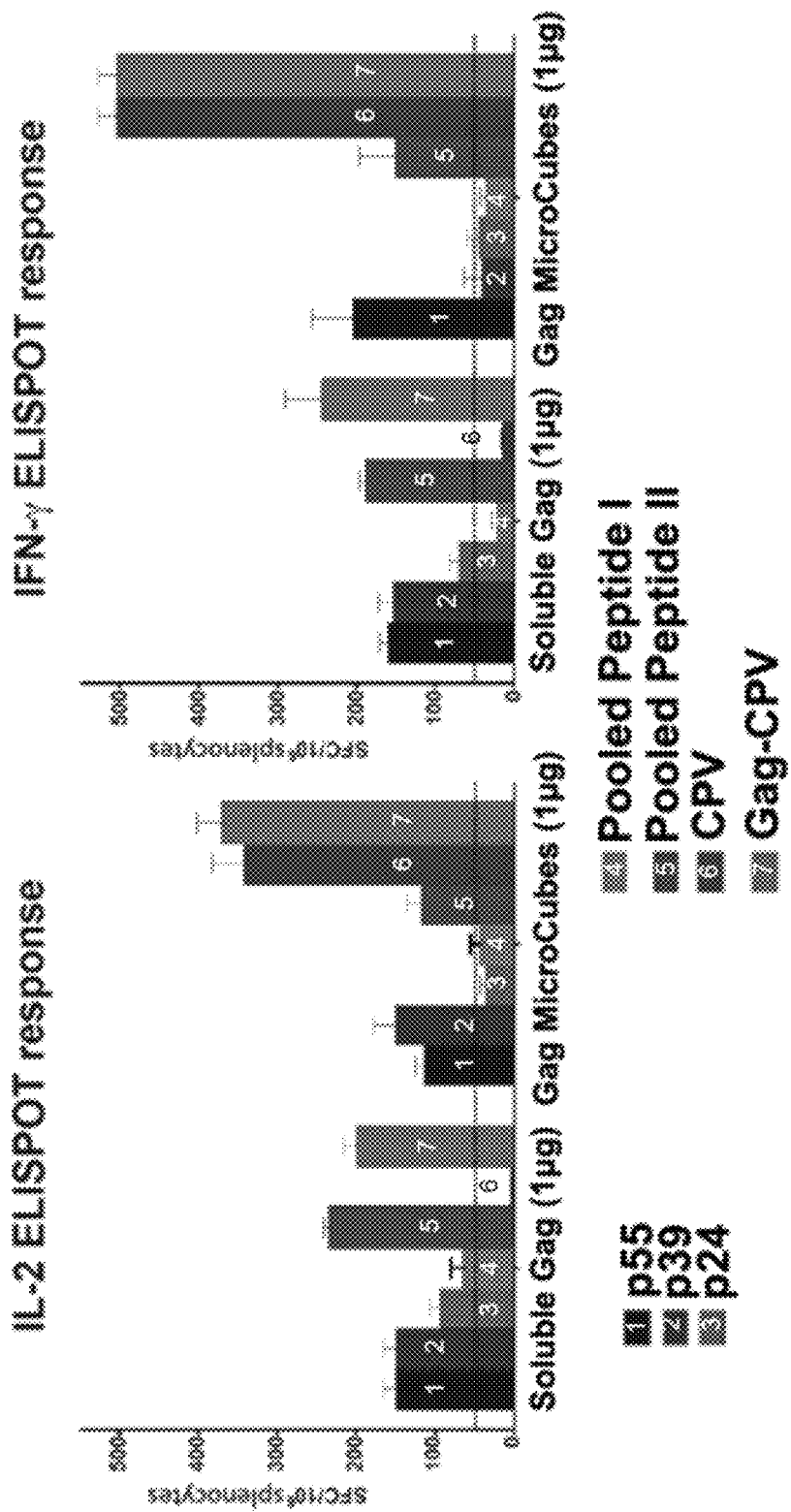

Gag MicroCubes are highly stable in the presence of trypsin (FIGS. 2A-2C) and under physiologically relevant conditions (FIGS. 3A and 3B).

The Gag protein incorporated in MicroCubes is more stable to trypsin degradation than soluble Gag suggesting that it will provide a stable complex and sustained release of antigen when injected in vivo.

EXAMPLE 6

Assessment Of Immunogenicity Of HIV Gag MicroCubes

Murine Immunogenicity
Aim

To investigate immunogenicity of the HIV-1 Gag Micro-Cubes in vivo, compared to soluble HIVgag protein, in a dose ranging study.
Study Design 6 BALB/c mice per group, immunized with 100 µl immunogen in PBS subcutaneously, at weeks 0, 4 and 8
Group A; High dose HIV gag MicroCubes (approx 450 µg, containing 5 µg HIVgag)
Group B; Mid dose HIV gag MicroCubes (approx 90 µg, containing 1.0 µg HIVgag)
Group C; Low dose HIV gag MicroCubes (approx 18 µg, containing 0.2 µg HIVgag)
Group D; High dose HIV gag soluble protein 5 µg
Group E; Mid dose HIV gag soluble protein 1.0 µg
Group F; Low dose HIV gag soluble protein 0.2 µg Venous blood is collected from animals at weeks 0 (pre-bleed), 4 and 8. Animals are sacrificed at week 10 when the spleens are taken for assessment of T cell responses to the immunogens, and a terminal heart bleed is performed for serum for antibody assessments.

Methods

T-cell responses are assessed in IFN-γ and IL-2 ELISPOT assays. Briefly, $5\times10^5$ spleen cells were added to wells coated with monoclonal antibodies to either murine IFN-γ or murine IL-2. These cells were stimulated with the following antigens; media alone as negative control, Con A as positive control, HIV gag soluble protein (10, 1.0, 0.1 μg/ml), HIV Gag MicroCubes (100, 10, 1.0 μg total protein), control protein (polyhedra crystals alone), HIV Gag overlapping peptide pools I and II (see FIG. 8) (source: NIH; 1 ug/ml final concentration each peptide).

After overnight incubation cells are removed and the ELISPOTs developed. Spot forming cells/$10^6$ input splenocytes are calculated using the AID ELISPOT imaging system.

Antibody responses to HIV gag was assessed using ELISA using recombinant HIV Gag soluble protein as antigen (Keoshkerian et al., *J. Med. Virol.* 71(4): 483-491, 2003; Dale et al., *Vaccine,* 23(2): 188-197, 2004; Thomson et al., *Vaccine,* 23(38): 4647-4657, 2005; Kelleher et al., *AIDS,* 20(2): 294-297, 2006).

Strong antibody responses to Gag were detected in both the soluble Gag and Gag MicroCube immunized mice. The maximal antibody titre of 1:25600 was observed for the 5.0 μg group with weaker responses at lower doses (see FIGS. 6A-6C and 7A-7D). HIV Gag MicroCube-immunized mice also demonstrated strong antibody responses to the CPV polyhedrin protein.

T-cell responses were assessed using IFN-γ and IL-2 ELISPOT assays. MicroCubes elicited very strong IFN-γ and IL-2 responses to Gag p55 (>500 SFC/$10^6$ cells). Slightly reduced responses were observed against the smaller fragments Gag p39 or p24. Peak IFN-γ responses were seen in the 1.0 μg group, with slightly lower responses at 5.0 μg. Importantly, higher IFN-γ responses were seen with 1.0 μg of the Gag MicroCubes (mean 210 SFC/$10^6$ cells) than with 1.0 μg gag (mean 150 SFC/$10^6$ cells). Strong IFN-γ responses to the CPV polyhedrin protein were also seen, but this was not observed in the IL-2 assay. Assays of responses to two pools of overlapping peptides corresponding to the N- and C-terminal regions of the HIV-1 Gag protein showed that the majority of the IFN-γ and IL-2 responses were directed to the second half of the protein.

The robust IFN-γ and IL-2 responses to the Gag protein and Gag peptides observed after injection with Gag MicroCubes imply that this vaccine elicits both CD4 and CD8 responses without the need for adjuvant.

EXAMPLE 7

Discussion

The present invention provides a vaccine platform against infectious diseases based on ultra-stable crystals or MicroCubes (polyhedra) produced by common insect viruses. MicroCubes present two features that set them apart from existing vaccine strategies: a novel presentation of antigens as a para-crystalline array and a unique slow-release delivery mechanism. In some embodiments, these qualities provide immunogenicity and stability. In some embodiments, MicroCubes are used in respect of diseases that require a vigorous cellular immune response, such as HIV or malaria. In other embodiments, MicroCubes are proposed for vaccination for the developing world by offering single-shot immunizations and reducing the need for a cold chain in vaccine supply.

One aspect of the invention is to employ the natural function of viral polyhedra, virus-containing crystals of the polyhedrin protein, that protect the particles of many insect viruses from environmental insults. The striking physicochemical stability of polyhedra means that the infectivity of the virus can be preserved in soil for years at ambient temperature. Recently, the much-anticipated structure of cypovirus polyhedra provided unprecedented opportunities to engineer these crystals to efficiently incorporate proteins derived from human pathogens in place of the virus particles throughout and on the surface of crystals. Herein, these crystals are referred to as "MicroCubes" owing to their shape and size (0.5-10 μm).

Subunit vaccines fail to elicit a strong cellular immune response necessary to protect against a number of major pathogens (e.g. HIV). Attenuated viruses are less safe and challenging—if not impossible—to engineer for many diseases (e.g. malaria). In contrast, MicroCubes are proposed to induce both humoral and cellular responses against a range of antigens because of an improved presentation of the antigen and their particulate nature. In addition, the highly multivalent presentation of the antigen and the slow-release delivery mechanism mean that the immune responses should also be much stronger and more sustained than any available subunit vaccine, even with single-shot immunizations.

To date, the advantages of symmetrical presentation of antigens have only been explored in specific examples that lack the potential of a generic vaccine platform. For instance, although very successful in the current papillomavirus vaccines (e.g. "Gardasil") and hepatitis B vaccines (e.g. "Engerix-B"), vaccines based on virus-like particles are not generally applicable especially when large or multiple antigens are required. In contrast, in some embodiments, MicroCubes are proposed to tolerate cargoes as large as whole virus particles and even multiple different antigens at once.

As shown herein, Gag MicroCubes induce a strong immune response including both a specific antibody production and a robust cell response when injected in mice. This could not be anticipated from background information as the crystals may have been rapidly cleared from the organism, or unable to be processed by antigen-presenting cells, or capable of inducing only either humoral or cellular responses.

EXAMPLE 8

Engineering Of Illustrative Antigen-Micro Cubes (Polyhedra)

MicroCubes can be Engineered to Efficiently Incorporate the HIV-1 Gag Protein

Six constructs of the Gag protein were cloned into a custom plasmid pDEST-H1 as N-terminal fusion with the Bm-CPV H1-tag. These constructs were the full-length p55 Gag protein of HIV-1 NL4.3, GagΔp6 and Gag-WM ($W_{316}M_{317}$/AA mutant reducing Gag dimerization). C-terminal $His_6$-tag fusions of each of these constructs were also engineered. Recombinant baculoviruses were obtained by cellfectin-mediated co-transfection of a modified pDEST-H1 vector and a linearised baculovirus genome (BaculoGold, Novagen). MicroCubes were produced by co-infection of Sf9 cells with the resulting high-titer baculovirus stocks and a baculovirus coding for the polyhedrin protein of Bm-CPV. MicroCubes are purified from infected cells by sonication and differential centrifugation as described in Ijiri et al., *Biomaterials* 30: 4297-4308, 2009. Western blot analysis of MicroCubes demonstrated the incorporation of the Gag protein in all constructs at similar levels. Subsequent experiments were all carried out using the full-length-$His_6$ construct (FIGS. 9A and 9B).

A time course revealed that Gag is incorporated into MicroCubes as early as 24 h post-infection. Incorporation levels increased at 48h and dramatically dropped beyond 72 h post-infection (data not shown). For vaccination purposes, MicroCubes were further purified on a 45-65% (w/w) sucrose step gradient. One or two distinct bands corresponding to the crystals were observed depending on the preparation. The resulting crystals were purified to homogeneity and only the Gag and Bm-CPV polyhedrin proteins was detected even on a grossly overloaded gel as confirmed by mass spectrometry (FIG. 9A). The upper band around 55 kDa was confirmed by peptide mass fingerprinting spectrometry to be a mixture of HIV-1 Gag and the Bm-CPV polyhedrin probably forming a SDS-resistant trimer. To increase the level of cargo protein in MicroCubes, the ratio of the two baculovirus stocks was varied at a constant total multiplicity of infection. A four-fold excess of the Gag baculovirus stock resulted in maximum incorporation levels. The ratio was estimated by semi-quantitative Western blot and a commercial p24 ELISA (NCI-Frederick). In optimal conditions, the ratio of polyhedrin protein versus Gag was 90:1 (w/w) or 170:1 (mol:mol). Electron microscopy (FIGS. 9C and 9D) demonstrated that no gross defect was introduced in the crystalline organization of MicroCubes by incorporation of the cargo molecule as anticipated from previous analysis (Coulibaly et al., *Nature,* 446: 97-101, 2007). Indeed, high-resolution diffraction of synchrotron X-ray was observed up to 2.4 Å from these crystals demonstrating the integrity of the crystalline matrix (data not shown).

MicroCubes can Incorporate Two Antigens Simultaneously

Co-expression with H1-EGFP to produced doubly-labeled MicroCubes. Fluorescent crystals were obtained (FIGS. 10A and 10B) and we developed a new FACS analysis was undertaken to quantify the degree of incorporation of both cargoes. 42% of MicroCubes were doubly-labeled (FIG. 10C) while 13% exhibited significant EGFP fluorescence but had no accessible Gag. These crystals may still have been dual expressing since the majority of Gag is embedded in the dense crystalline matrix and cannot be detected by incubation with anti-Gag antibody on intact MicroCubes. A total of 38% of the crystals have no cargo. In conclusion, 1) Dual MicroCubes can be readily produced even when using a common H1-tag and 2) FACS emerges as a powerful tool to characterize and sort MicroCubes.

EXAMPLE 9

Immunogenicity Study Of Antigen Micro Cubes In A Murine Model

Antigen MicroCubes are Safe and Highly Immunogenic in Mice

Highly purified crystals were shown to be sterile (NATO-accredited sterility test; Silliker Australia) and free of significant LPS contamination (<0.02 EU per injection; Limulus Amebocyte Lysate assay; Cambrex). To investigate immunogenicity of Antigen MicroCubes, groups of 8 BALB/c mice were immunized subcutaneously with high (equivalent to 5 μg of Gag), medium (1 μg) or low dose (0.2 μg) of the immunogen in PBS at weeks 0, 4 and 7. Three control groups received the same doses of recombinant Gag purified from *E. coli.* Venous blood was collected from animals at weeks 0 (pre-bleed), 4 and 8. Animals were sacrificed at week 10 when the spleens were taken for assessment of T cell responses to the immunogens.

Strong Gag-specific, dose-escalating humoral responses were observed for soluble Gag and Gag MicroCubes as assessed by ELISA against recombinant Gag. Maximal antibody titres of $2.6\times10^4$ (soluble Gag) and $1.3\times10^4$ (Gag MicroCubes) were measured for the 5.0 μg groups (FIG. 11A). Gag MicroCube-immunized mice also demonstrated strong antibody responses to the polyhedrin protein forming the crystalline matrix.

Gag MicroCubes also elicited very strong T-cell responses measured by IFN-γ and IL-2 ELISPOT responses to Gag p55 (>200 SFC/$10^6$ cells) and slightly weaker responses against the p39 or p24 domains of Gag. Peak IFN-γ responses were seen in the 1.0 μg group, with slightly lower responses at 5.0 μg. Higher IFN-γ responses were seen with 1.0 μg of the Gag MicroCubes (mean 205 SFC/$10^6$ cells) than with 1.0 μs soluble Gag (mean 160 SFC/$10^6$ cells) (FIG.

11B). Responses to the CPV polyhedrin protein were also very strong especially in the IFN-γ assay. Assays of responses to two pools of overlapping peptides corresponding to the N- and C-terminal regions of the Gag protein showed that the majority of the IFN-γ and IL-2 responses were directed to the second-half of the protein.

T-cell responses to soluble Gag were also strong and indeed comparable to those of MicroCubes, contrary to the initial hypothesis. This hypothesis assumed that unadjuvanted recombinant protein would not induce significant cellular responses. However the robust cellular and humoral responses seen here can be explained here by the particulate nature of this preparation of recombinant Gag which is known to form aggregates and VLPs in the condition of injection. In addition, slightly higher LPS levels (0.04 vs. <0.02 EU/injection for MicroCubes) were consistently observed in soluble Gag produced in E. coli rather than insect cells. Contaminating LPS may also have acted as mild adjuvant thereby enhancing the responses induced by recombinant Gag.

In conclusion, the robust Gag-specific IFN-γ and IL-2 responses, and high titre antibody responses, observed after immunization with Gag MicroCubes demonstrate that this vaccine elicits strong cellular and humoral immunity without the need for adjuvant. This proof-of-concept provides a solid basis to investigate the magnitude of these responses in comparison with established vaccine strategies.

EXAMPLE 10

Distinctive Features Of Micro Cubes: Robustness And Self-adjuvanting Properties

MicroCubes Protect Antigen Against Proteolytic Degradation and Heat Denaturation. Due to the natural robustness of polyhedra and their protective function in the viral cycle, it was hypothesized that cargoes in MicroCubes would be protected from degradation. To test this idea, MicroCubes were incubated at various temperatures and analysed by Western blot to monitor the levels and integrity of the Gag protein. Freezing at −20° C. and freeze-drying were initially investigated. Minor losses were observed and these conditions of storage were avoided in subsequent experiments. This was attributed to increase adherence to the plastic tube which was particularly obvious after freeze-dry where a white film of MicroCubes was clearly deposited on the side of the tube (data not shown).

Figure 12A:
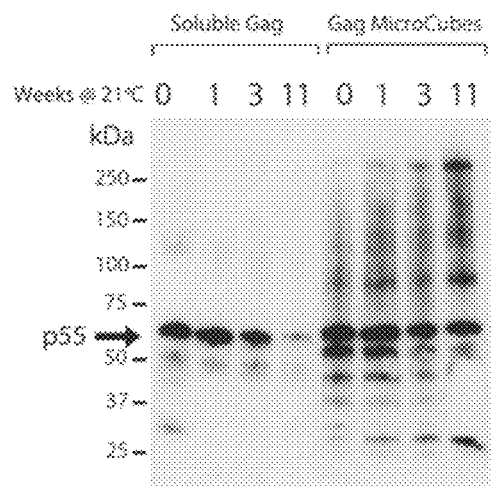
FIGS. 12A-12D are photographical representations of data showing Gag in MicroCubes is protected from heat denaturation and proteolytic degradation.

In contrast, Gag MicroCubes were found to be highly stable between 4° C. and 21° C. and even at 37° C. A comparison with soluble Gag is presented in FIG. 12A. Degradation of soluble Gag is apparent at week 3 and virtually complete at week 11. In stark contrast, Gag in MicroCube is completely protected for at least 11 weeks (FIG. 12A).

At 37° C., the highest temperature of this set of experiments, an intermediate situation was observed. Gag initially appeared to be completely protected but started to degrade from day 4 and became eventually undetectable by day 14 (data not shown). Further experiments were carried out to try to identify the cause of Gag degradation in MicroCubes and try to prevent it.

Figure 12B:
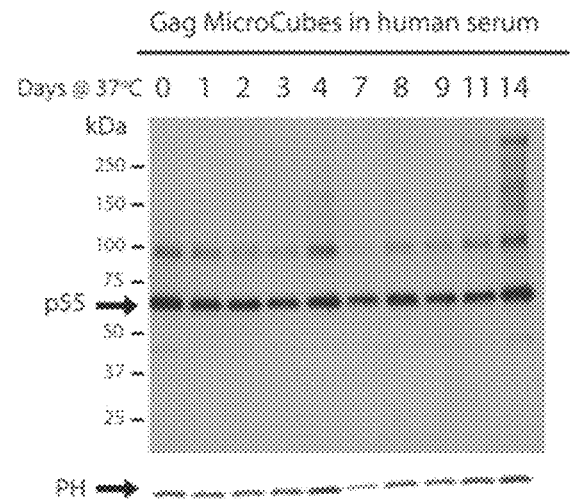
Figure 12C:
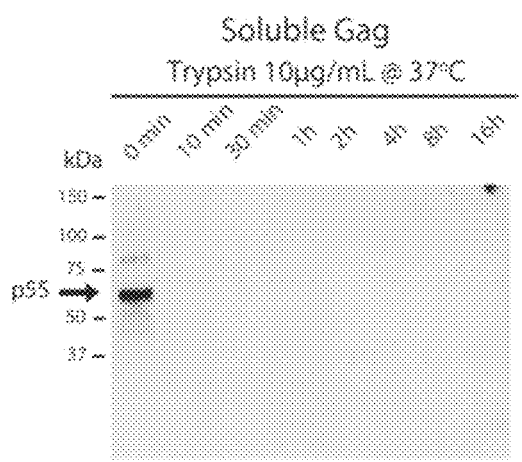
Figure 12D:
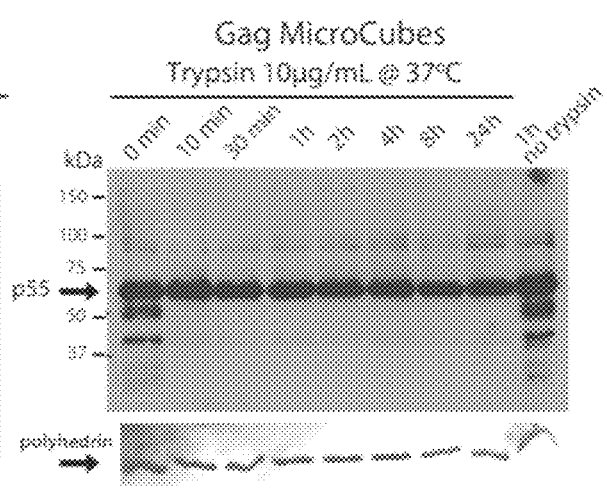

First, the susceptibility of Gag to proteolytic degradation was investigated. As expected, soluble Gag was found to be extremely sensitive to trypsin degradation: the incubation of 10 μg of soluble Gag at 37° C. with trypsin (10 μg/mL) resulted in complete loss of Gag in less than 10 min (FIG. 12C). However, when Gag MicroCubes were incubated in the same experimental conditions and analysed by Western blot, only smaller fragments of Gag appeared to be susceptible to degradation while the intensity of the bands corresponding to full-length Gag remained constant even after 24h of incubation at 37° C. (FIG. 12D). Thus, it appears that part of the Gag protein is presented at the surface of MicroCubes and rapidly degraded by trypsin, while Gag embedded within the crystalline matrix is inaccessible and perfectly protected from proteolytic degradation. This experiment also implies that proteolytic degradation is not the reason for the loss of Gag from MicroCube observed at 37° C. Indeed, similar losses of Gag was observed at 37° C. even when broad-spectrum protease inhibitors (Roche Complete tablets) are added. No further stabilization was achieved with sodium azide but addition of serum resulted in improvement in stability. In human serum, Gag MicroCubes were found to be stable for at least 14 days at 37° C. in the absence of any other additive (FIG. 12B).

In conclusion, when embedded in MicroCubes, the Gag protein is protected from proteolytic degradation and stable for the duration of the experiment (11 weeks) between 4° C. and 21° C. Gag is also stable when incubated at 37° C. if serum is added and the overall stability of Gag MicroCubes appears very promising for a vaccine tailored for the developing world. Fine characterization of MicroCube protective capacities is investigated in using stabilising additives, different crystal formulations and incubations closer to field conditions.

Figure 13A:
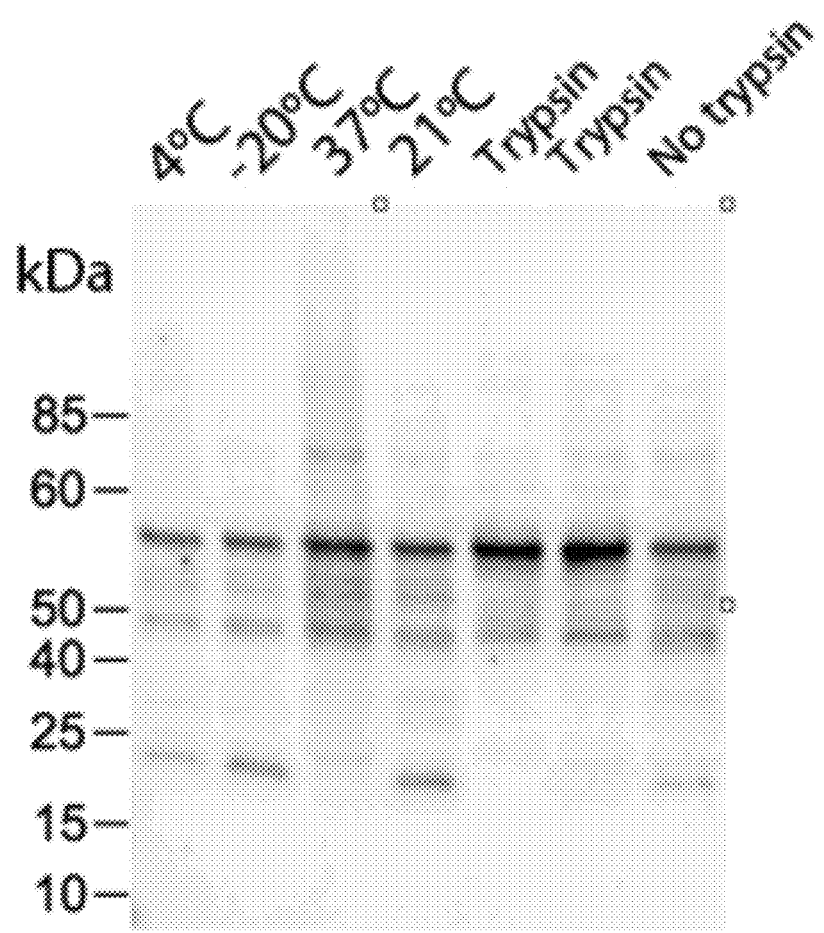
FIGS. 13A and 13B illustrate the immunogenicity of Gag MicroCubes is preserved at 21° C. and after incubation with trypsin.
Figure 13B:
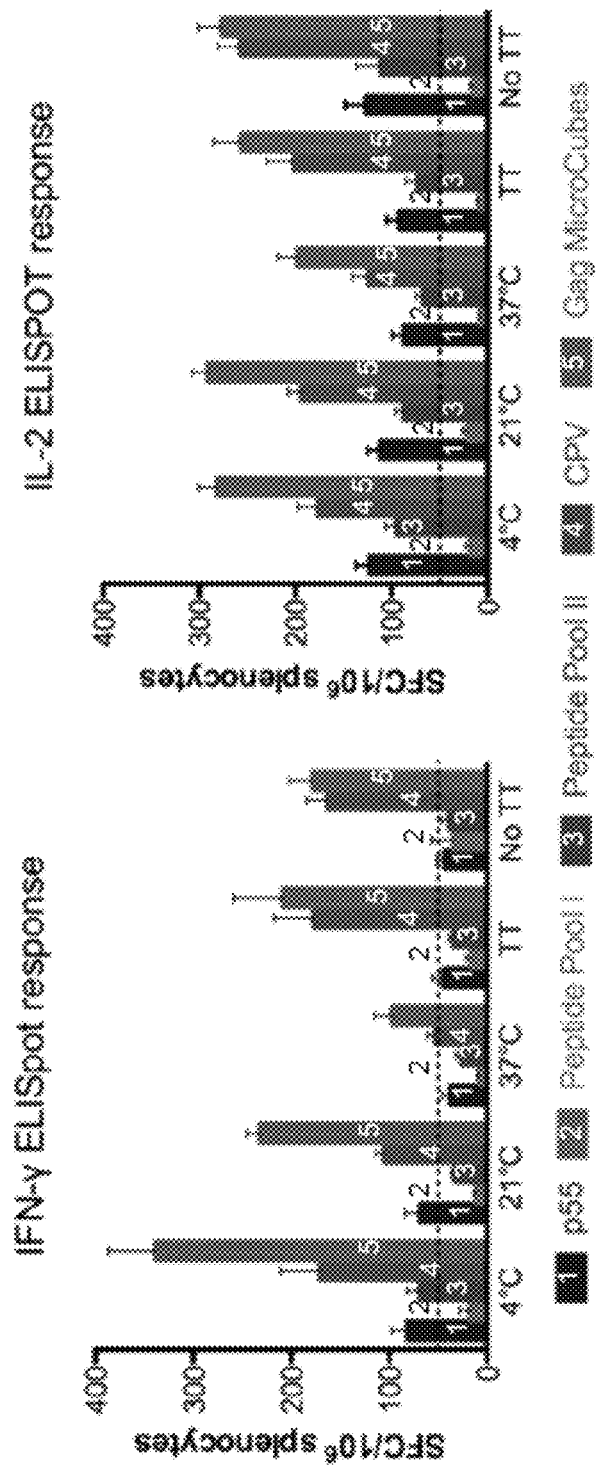

Antigen MicroCubes Retain their Immunogenicity After Prolonged Storage at 21° C. and Trypsin Treatment Immunogenicity studies were performed on BALB/c mice that received three subcutaneous immunizations with Gag MicroCubes (week 0, 4 and 6; 1 μg equivalent Gag) previously incubated at 4° C., 21° C. or 37° C. for a week or trypsin treated for an hour (FIG. 13A). Strong antibody response was observed for all groups, with a slightly higher titre for the 4° C. group (data not shown). The 4° C. and 21° C. groups both generated comparable T-cell responses (FIG. 13B) while the 37° C. group showed similar IL-2 responses but lower IFN-γ responses to all antigens. In comparison to the control groups (noTT), the groups immunized with trypsin-treated (TT) Microcubes showed only a slight drop of Gag-specific T-cell responses visible in the IL-2 ELISPOT responses. Thus, trypsin treatment of Gag MicroCubes demonstrated that the surface antigen protein is not essential to the humoral and cellular responses. This highlights the fundamentally different packaging of Gag into the 3-dimensional crystalline matrix of MicroCubes compared to the surface presentation found in classical virus-like particles. Further, antigen physically internal to the administered MicroCube is presented to the immune system indicates that surface antigen is not required although it may of course be present. Strong humoral and cellular responses were observed in both the 4° C. and 21° C. immunized groups which indicates that MicroCubes retain their ability to generate robust immune responses after a week at ambient conditions.

EXAMPLE 11

Presentation Of Antigens To Human T-Cells

Figure 14:
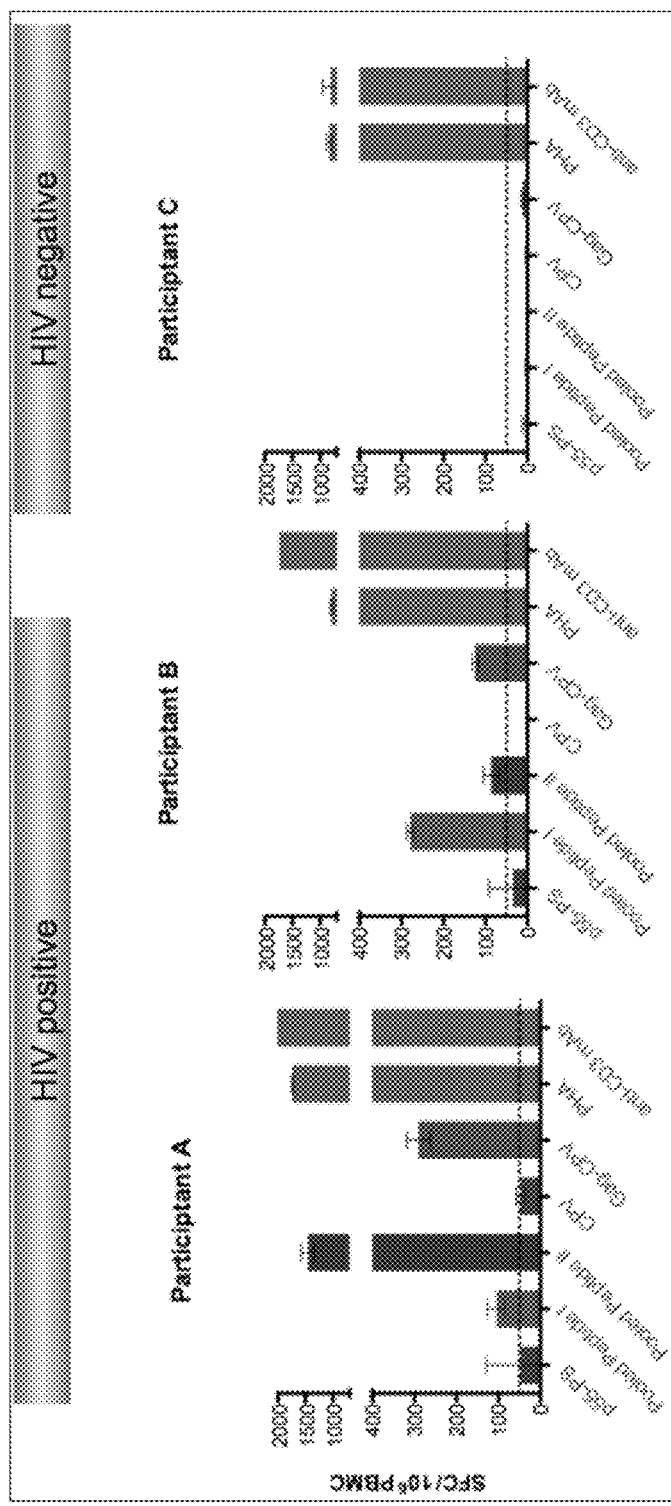
FIG. 14 is a graphical representation of data showing restimulation of human T-cells by Gag MicroCubes. PBMCs were isolated from HIV-positive donors (participants A and B) and HIV-negative donor (participant C) and re-stimulated with peptides, protein (p55) or MicroCubes (Gag-CPV or CPV), controls included PHA and anti-CD3. IFN-γ T-cell responses were measured by ELISpot analysis and plotted as a response per $1 \times 10^6$ cells.

IFN-γ and IL-2 ELISPOT assays were used to assess in vitro the ability of naturally induced HIV-specific T cells from HIV positive subjects to recognize Gag expressed within MicroCubes. We used Peripheral Blood Mononuclear Cells from HIV positive subjects and tested them for recognition of control and Gag MicroCubes, recombinant Gag protein and overlapping peptides. Strong positive responses to Gag MicroCubes was observed in 4 out of 6 subjects who had Gag T-cell responses, as determined by positive responses to Gag proteins or peptides (data not shown). The results for two HIV positive donors (A, B) and one HIV negative donor (C) are presented in FIG. 14. Cells were re-stimulated in vitro with HIV Gag peptides, the soluble Gag protein (p55) or MicroCubes (Gag-CPV or CPV). Strong IFN-γ responses to the peptide pool and Gag Micro-Cubes were only detected in the HIV-positive samples (FIG. 14). This demonstrates that Gag MicroCubes can be taken-up, processed by antigen-presenting cells and HIV epitopes correctly presented to T-cells isolated from HIV-positive donors.

EXAMPLE 12

MicroCubes Induce Release Of Mature IL-1β in Human PBMCs

The NALP3 inflammasome recognizes crystalline material appearing in joint fluids as a danger signal. Silica and Alum crystals have recently been demonstrated to exert their inflammatory and immunogenic properties via activation of the NALP3 inflammasome (Hornung et al., *Nat. Immunol.* 9(8):847-856, 2008). It was hypothesized that MicroCubes exert at least part of its adjuvant properties via crystalline activation of the inflammasome to induce IL1β.

Figure 15A:
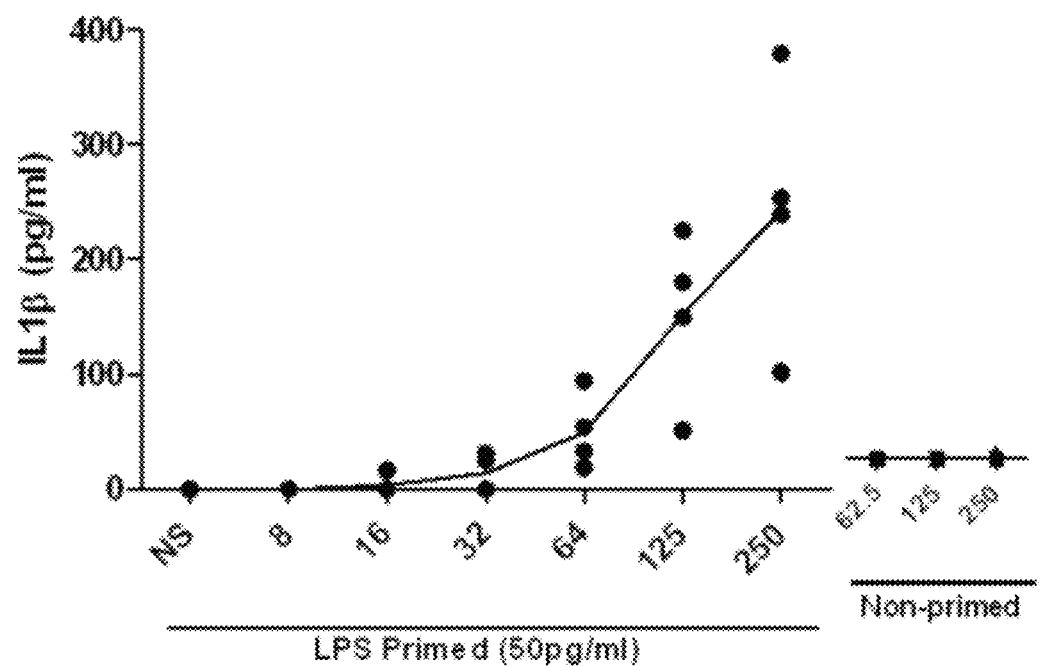
FIGS. 15A-15D are graphical representations of data showing MicroCubes induce release of IL-1β in human PBMCs in a caspase-1 dependent manner and requires phagocytosis.
Figure 15B:
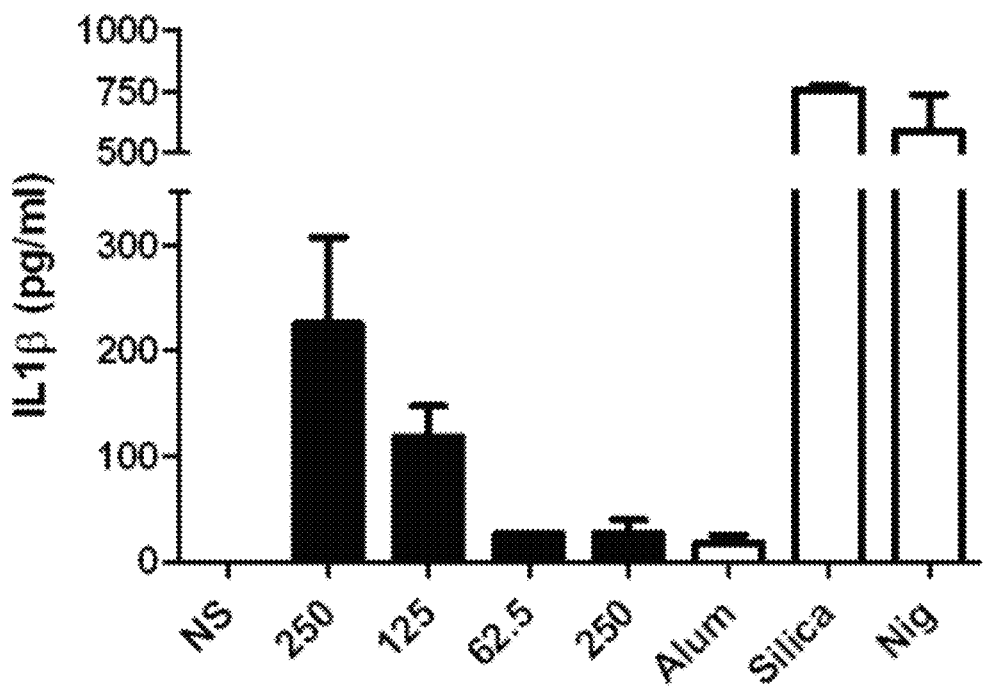
Figure 15C:
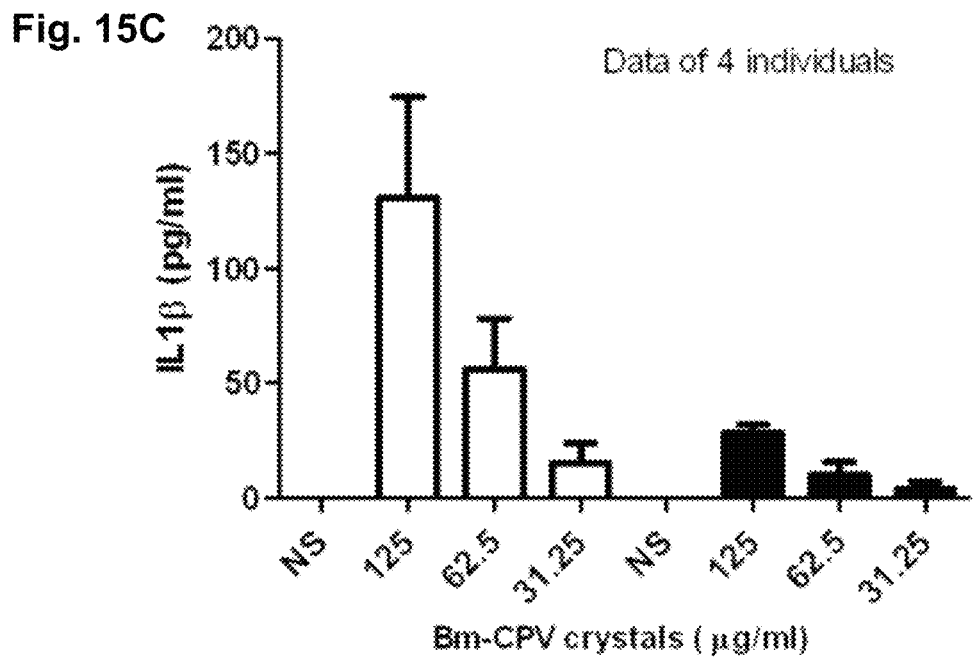

Human PBMCs from several donors were incubated with purified MicroCubes. Pro-IL-1β is not constitutively expressed and requires transcriptional induction in response to e.g. a TLR stimulus. MicroCubes did not induce IL-1β cleavage and release in human PBMCs by themselves, however, LPS-primed PBMCs strongly responded to the addition of MicroCubes in a dose-dependent manner (FIG. 15A). MicroCube-mediated activation of human PBMCs was as potent as other known activators of the NALP3 inflammasome, such as Alum, Silica crystals, or Nigericin (FIG. 15B). Inhibition of caspase-1 by the specific peptide inhibitor z-YVAD almost completely abolished the IL-1β response in response to MicroCube treatment (FIG. 15C). These data suggest that MicroCubes activate IL-1β in a caspase-1 dependent manner in human immune cells.

Figure 15D:
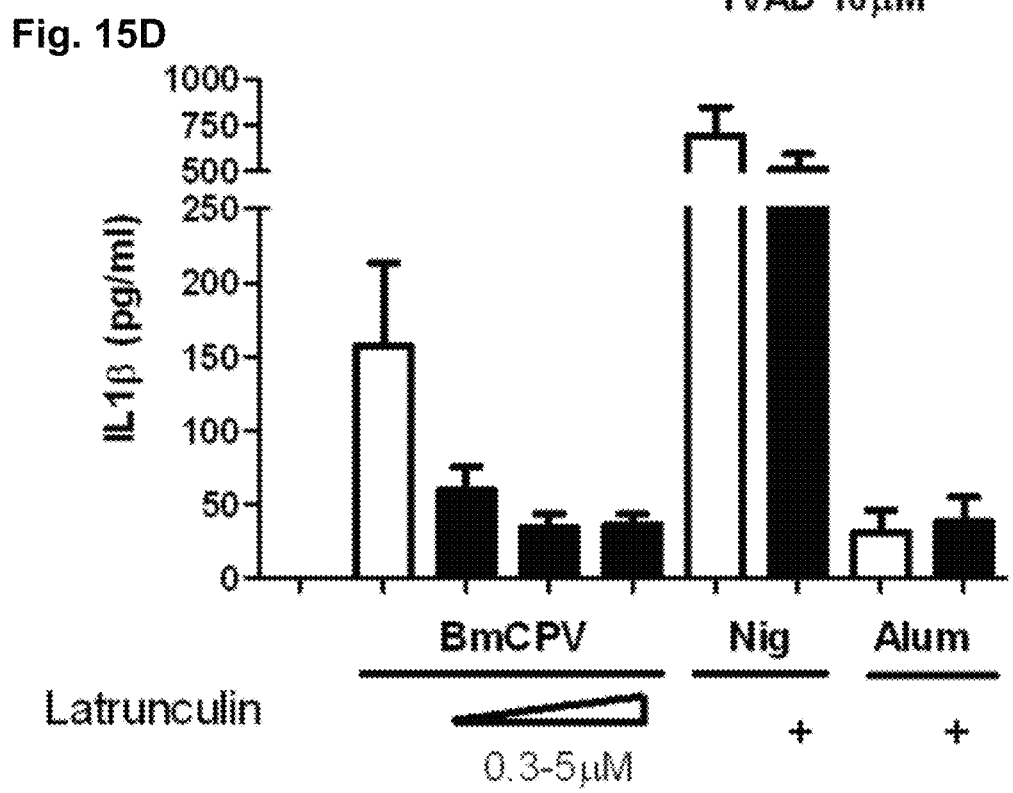

In order to decipher the upstream mechanisms involved in MicroCube-induced IL-β secretion, it was tested whether or not uptake of crystalline inflammasome activators influenced cell activation. Human PBMCs were pretreated with Latrunculin A, an inhibitor of phagocytosis, which impairs actin filament assembly and subsequently stimulated with MicroCubes as well as with the non-crystalline NALP3 activator, Nigericin. Latrunculin A potently inhibited IL-1β release following MicroCubes while the response to Nigericin was unaffected (FIG. 15D).

EXAMPLE 13

MicroCubes Activate The NALP3 Inflammasome

Figures 16A, 16B:
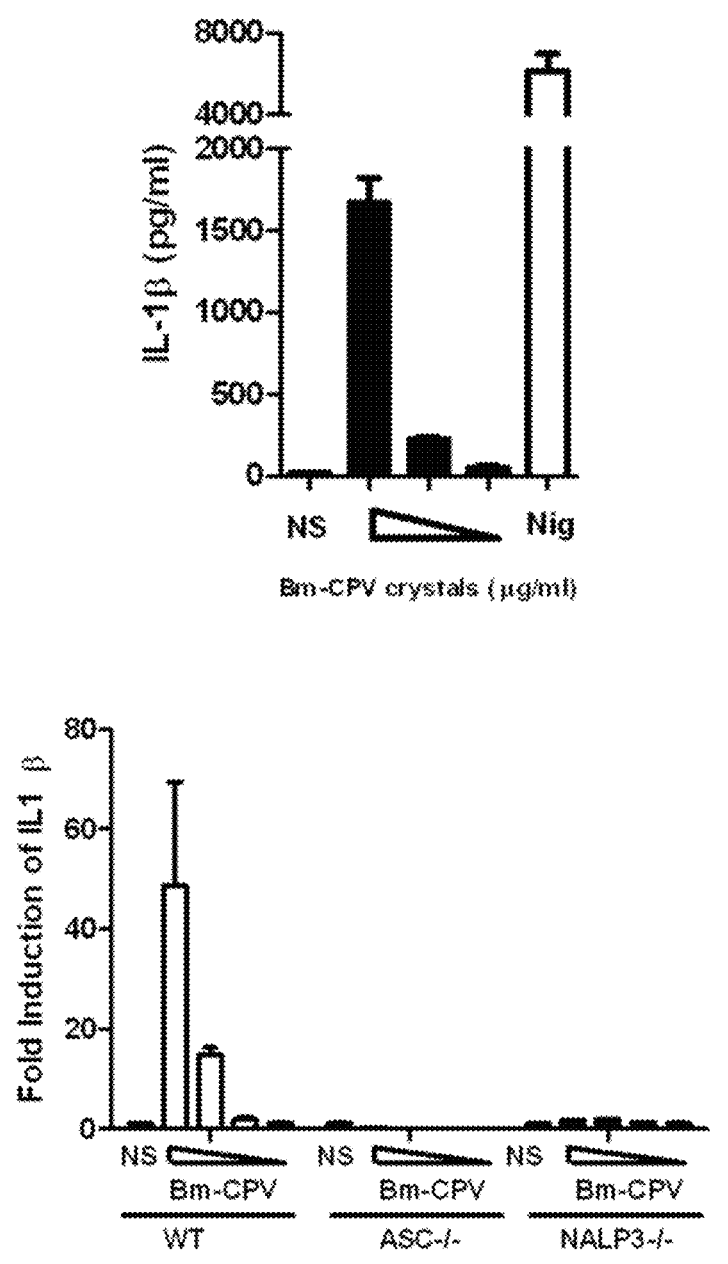

In order to investigate whether MicroCubes can activate the NALP3 inflammasome, experiments were performed in immortalized murine macrophages from mice deficient in NALP3 or ASC (Hornung et al. supra). Macrophages from wild-type mice produced large amounts of IL-1β following treatment with descending amounts of MicroCube exposure (FIG. 16A). In contrast, macrophages lacking NALP3 or the downstream adapter molecule ASC, failed to release comparable cleaved IL-1β in response to MicroCubes (FIG. 16B), indicating the requirement of NALP3 and ASC for IL-1β processing upon MicroCube exposure. Collectively, these results clearly suggest that silica crystals activate the NALP3/ASC complex leading to the activation of caspase-1 and subsequent cleavage of pro-IL-1β into mature, secreted IL-1β.

Overall, these results clearly demonstrate that Micro-Cubes activate the ASC/NALP3 inflammasome producing mature IL1β in a phagocytosis-dependent manner. The inflammasome activation may have potent proinflammatory effects in vivo which could account for at least part of the auto-adjuvant effect of MicroCube stimulation observed in the murine experiments.

Many modifications will be apparent to those skilled in the art without departing from the scope of the present invention.

TABLE 1

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 2

Exemplary and Preferred Amino Acid Substitutions

| Original residue | Exemplary substitutions | Preferred substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

BIBLIOGRAPHY

Altschul et al., *Nucl. Acids Res.,* 25: 3389-3402, 1997
Arkin and Yourvan, *Proc. Natl. Acad. Sci. USA,* 89: 7811-7815, 1992
Ausubel et al., *Cell Immunol.,* 193(1): 99-107, 1999

Ausubel et al., *Current Protocols in Molecular Biology*, John Wiley & Sons Inc, Chapters 10, 15-16, Unit 19.3 and pages 2.10.1 to 2.10.16, 1994-1998
Bird, *Science* 242:423, 1988
Carter et al., *Bio/Technology* 10:163-167, 1992
Carter et al., *Proc. Nat. Acad. Sci.* 89:4285 1992
Clackson et al., *Nature* 352:624-628, 1991
Coligan et al., *Current Protocols in Protein Science*, John Wiley & Sons, Inc., Chapters 1, 5 and 6, 1995-1997,
Colowick and Kaplan, eds., *Methods In Enzymology*, Academic Press, Inc.
Coulibaly et al., *Nature*, 446: 97-101, 2007
Coulibaly et al., *Proc. Natl. Acad. Sci. U.S.A.* 106(52): 22205-22210, 2009
Dale et al., *Vaccine*, 23(2): 188-197, 2004
Dayhoff et al., *Atlas of Protein Sequence and Structure*, Natl. Biomed. Res. Found., Washington, D.C., Vol. 5, pp. 345-358, 1978
Delgrave et al., *Protein Engineering*, 6: 327-331, 1993
Deveraux et al., *Nucleic Acids Research* 12: 387-395, 1984
Fields and Knipe, eds, *Fundamental Virology*, 2nd Edition, 1991
Fields et al., eds, *Virology*, 3rd Edition, Lippincott-Raven, Philadelphia, Pa., 1996
Gonnet et al., *Science*, 256(5062): 1443-1445, 1992
Hornung et al., *Nat Immunol.*, 9(8): 847-856, 2008
Huston et al., *Proc. Natl. Acad. Sci. USA* 85:5879, 1988
Ijiri et al. *Biomaterials* 30: 4297-4308, 2009
Ikeda et al., *J. Virol.* 75: 988-995, 2001
Ikeda et al., *Proteomics*, 6: 54-66, 2006
Joklik ed., *Virology*, 3rd Edition, 1988
Jones et al., *Nature* 321:522-525, 1986
Kabat et al in *Sequences of Proteins of Immunological Interest*, 5th Ed., US Department of Health and Human Services, PHS, NIH, NIH Publication No. 91-3242, 1991
Kelleher et al., *AIDS*, 20(2): 294-297, 2006
Keoshkerian et al., *J. Med. Virol.* 71(4): 483-491, 2003
Kohler and Milstein, *Nature* 256:495-499, 1975
Kortt et al., *Protein Engineering* 10:423, 1997
Kunkel et al., *Methods in Enzymol.*, 154: 367-382, 1987
Kunkel, *Proc. Natl. Acad. Sci. USA*, 82: 488-492, 1985
Larrick et al., *Bio/Technology* 7:934, 1989
Liu et al., *Proc. Natl. Acad. Sci. USA* 84:3439, 1987
Marks et al., *J. Mol. Biol.* 222:581-597, 1991
Mori et al., *J. Biol. Chem.* 282(23): 17289-17296, 2007
Mori et al., *J. Gen. Virol.* 74(1): 99-102, 1993
Morrison et al., *Proc. Nat. Acad. Sci.* 81:6851, 1984
Newton and Graham eds., *PCR, Introduction to Biotechniques Series*, 2nd ed., Springer Verlag, 1997
Atherton and Shephard (supra), Chapter 9
Padlan et al., *Mol. Immunol.* 28:489-498, 1991
Pedersen et al., *J. Mol. Biol.* 235:959-973, 1994
Presta, *Curr. Op. Struct. Biol.* 2:593-596, 1992
Ream et al., eds., *Molecular Biology Techniques: An Intensive Laboratory Course*, Academic Press, 1998
Reichmann et al., *Nature* 332:323-329, 1988
*Remington's Pharmaceutical Sciences*, 18th Ed., Mack Publishing, Company, Easton, Pa., U.S.A., 1990
Rice-Ficht et al., *Current Opinion in Microbiology*, 13: 106-112, 2010
Roberge et al., *Science*, 269(5221): 202-204, 1995
Sambrook et al., *Molecular Cloning: A Laboratory Manual*, Cold Spring Harbor Laboratory, Cold Spring Harbor, N.Y., Sections 1.101 to 1.104, 16 and 17, 1989
Thomson et al., *Vaccine*, 23(38): 4647-4657, 2005
Tomizuka et al., *Proc. Natl. Acad. Sci. USA* 97: 722-727, 2000
Ward et al., *Nature* 334:544, 1989
Watson et al., *Molecular Biology of the Gene, Fourth Edition*, Benjamin/Cummings, Menlo Park, Calif., 1987
Weir and Blackwell, eds., *Handbook of Experimental Immunology, Vols. I-IV*, Blackwell Scientific Publications, 1986
Winter & Harris, *TIPS* 14: 139, 1993
Yu et al., *Nature*, 453(7193): 415-419, 2008
Zubay, G., *Biochemistry*, third edition, Wm.C. Brown Publishers, 1993

The invention claimed is:

1. A method of eliciting an immune response in a subject or patient, the method comprising administering to the subject or patient an effective amount of a pharmaceutical composition under conditions to elicit an immune response, wherein:
   the pharmaceutical composition comprises a complex in an amount that induces an immune response in a subject; and
   the complex comprises:
   an antigen of a pathogen or other antigen against which an immune response is sought in a human or non-human animal subject; and
   a polyhedrin protein derived from a cytoplasmic polyhedrosis virus (CPV), whereby delivery of the complex to a subject in substantially particulate polyhedral form induces an immune response thereto.

2. A method of immunizing a subject against infection or disease or a condition associated with an antigen, comprising administering to the subject a pharmaceutical composition, wherein:

the pharmaceutical composition comprises a complex in an amount that induces an immune response in a subject; and the complex comprises:

an antigen of a pathogen or other antigen against which an immune response is sought in a human or non-human animal subject; and a polyhedrin protein derived from a cytoplasmic polyhedrosis virus (CPV), whereby delivery of the complex to a subject in substantially particulate polyhedral form induces an immune response thereto.

3. A method of treating infection by a pathogen or a cancer or disease or other condition, comprising administering to the subject a pharmaceutical composition for a time and under conditions sufficient to treat the infection or cancer or disease or condition, wherein:

the pharmaceutical composition comprises a complex in an amount that induces an immune response in a subject; and the complex comprises:

an antigen of a pathogen or other antigen against which an immune response is sought in a human or non-human animal subject; and a polyhedrin protein derived from a cytoplasmic polyhedrosis virus (CPV), whereby delivery of the complex to a subject in substantially particulate polyhedral form induces an immune response thereto.

4. A method for producing an isolated or purified antibody or immune cell that specifically binds to an antigen of a pathogen or other antigen against which an immune response is sought in a human or non-human animal subject or patient, comprising administering to a subject an effective amount of a pharmaceutical composition, wherein:

the pharmaceutical composition comprises a complex in an amount that induces an immune response in a subject; and the complex comprises:
- an antigen of a pathogen or other antigen against which an immune response is sought in a human or non-human animal subject; and
- a polyhedrin protein derived from a cytoplasmic polyhedrosis virus (CPV), whereby delivery of the complex to a subject in substantially particulate polyhedral form induces an immune response thereto;

and isolating or purifying an antibody or immune cell of the immune response.

5. The method of claim 1, wherein the antigen is fused to a polyhedrin targeting peptide.

6. The method of claim 5, wherein the targeting peptide is derived from the N-terminal H1 α-helix of a CPV polyhedrin protein.

7. The method of claim 1, wherein, when the antigen is in the polyhedra, its heat stability is increased compared to the antigen in the absence of the polyhedra.

8. The method of claim 1, wherein the antigen in the polyhedra displays decreased degradation.

9. The method of claim 1, wherein the antigen is IIIV gag protein.

10. The method of claim 1, wherein the antigen is fused to a CPV polyhedrin peptide.

11. The method of claim 1, wherein the antigen is an antigen from a pathogen.

12. The method of claim 1, wherein the polyhedrin protein is *Bombyx mori* CPV polyhedrin.

13. The method of claim 1, wherein the pharmaceutical composition further comprises an adjuvant.

* * * * *

UNITED STATES PATENT AND TRADEMARK OFFICE
CERTIFICATE OF CORRECTION

PATENT NO. : 10,682,407 B2  
APPLICATION NO. : 15/232736  
DATED : June 16, 2020  
INVENTOR(S) : Coulibaly et al.

Page 1 of 2

It is certified that error appears in the above-identified patent and that said Letters Patent is hereby corrected as shown below:

On the Title Page

In Item (56) References Cited, in OTHER PUBLICATIONS, on page 2, 1st Column, please replace "4,873,192 A 10/1989 Kunkel et al." with —4,873,192 A 10/1989 Kunkel—;

In Item (56) References Cited, in OTHER PUBLICATIONS, on page 2, 1st Column, please replace "7,282,353 B2 10/2007 Chao" with —7,282,353 B2 10/2007 Chao et al.—;

In Item (56) References Cited, in OTHER PUBLICATIONS, on page 2, 1st Column, please replace "7,319,000 B1 1/2008 Sastry" with —7,319,000 B1 1/2008 Sastry et al.—;

In Item (56) References Cited, in OTHER PUBLICATIONS, on page 2, 1st Column, please replace "7,619,060 B2 1/2009 Ikeda" with —7,619,060 B2 11/2009 Ikeda—;

In Item (56) References Cited, in OTHER PUBLICATIONS, on page 2, 1st Column, please replace "2006/0155114 A1 7/2006 Ikeda et al." with —2006/0155114 A1 7/2006 Ikeda—;

In Item (56) References Cited, in OTHER PUBLICATIONS, on page 2, 2nd Column, Line 43, please replace "97-101" with —97-101 (2007)—;

In Item (56) References Cited, in OTHER PUBLICATIONS, on page 3, 1st Column, Line 15, please replace "EMBO J. 29(2):505-514,2010)" with —EMBO J. 29(2):505-514 (2010)—;

In Item (56) References Cited, in OTHER PUBLICATIONS, on page 3, 1st Column, Lines 17-18, please replace "Nature 321(6069): 522-525 (986)" with —Nature 321(6069): 522-525 (1986)—;

In Item (56) References Cited, in OTHER PUBLICATIONS, on page 3, 1st Column, Line 26, please replace "Nature 256: 495-499 (975)" with —Nature 256: 495-497 (1975)—;

Signed and Sealed this  
Eleventh Day of October, 2022

Katherine Kelly Vidal  
*Director of the United States Patent and Trademark Office*

CERTIFICATE OF CORRECTION (continued)
U.S. Pat. No. 10,682,407 B2

In Item (56) References Cited, in OTHER PUBLICATIONS, on page 3, 1st Column, Line 52, please replace "polyhedera" with —polyhedra—;

In Item (56) References Cited, in OTHER PUBLICATIONS, on page 3, 1st Column, Line 68, please replace "489-498" with —489-498 (1991)—;

In the Specification

At Column 30, Line 22, please replace "DDH$_2$0" with —DDH$_2$O—;

At Column 33, Line 29, Column 34, Line 34, and Column 35, Line 31, please replace "Micro Cubes" with —MicroCubes—;

In the Claims

Please replace Claim 9 with the following amended claim:
—9. The method of claim 1, wherein the antigen is HIV gag protein.—.